(12) United States Patent
Ruecroft et al.

(10) Patent No.: US 9,637,840 B2
(45) Date of Patent: May 2, 2017

(54) PROCESS FOR IMPROVING CRYSTALLINITY

(75) Inventors: Graham Ruecroft, Oxford (GB); Dipesh Parikh, Oxford (GB); David Hipkiss, Oxford (GB)

(73) Assignee: Prosonix Limited (GB)

( * ) Notice: Subject to any disclaimer, the term of this patent is extended or adjusted under 35 U.S.C. 154(b) by 465 days.

(21) Appl. No.: 13/054,532

(22) PCT Filed: Jul. 20, 2009

(86) PCT No.: PCT/GB2009/050885
§ 371 (c)(1),
(2), (4) Date: Mar. 11, 2011

(87) PCT Pub. No.: WO2010/007447
PCT Pub. Date: Jan. 21, 2010

(65) Prior Publication Data
US 2011/0146678 A1    Jun. 23, 2011

(30) Foreign Application Priority Data

Jul. 18, 2008 (GB) .................................. 0813114.6
Apr. 9, 2009 (GB) .................................. 0906144.1
Jun. 3, 2009 (GB) .................................. 0909486.3

(51) Int. Cl.
| | | |
|---|---|---|
| B32B 5/16 | (2006.01) | |
| C30B 29/60 | (2006.01) | |
| A61K 9/00 | (2006.01) | |
| B01D 9/00 | (2006.01) | |
| C30B 1/12 | (2006.01) | |

(52) U.S. Cl.
CPC ............ *C30B 29/605* (2013.01); *A61K 9/008* (2013.01); *A61K 9/0075* (2013.01); *B01D 9/0027* (2013.01); *B01D 9/0081* (2013.01); *C30B 1/12* (2013.01); *Y10T 428/2982* (2015.01)

(58) Field of Classification Search
USPC .............................................. 117/5; 428/402
See application file for complete search history.

(56) References Cited

U.S. PATENT DOCUMENTS

| 8,034,381 | B2 | 10/2011 | Moschwitzer | |
| 2003/0051659 | A1* | 3/2003 | Rauls et al. .................... | 117/68 |
| 2003/0223939 | A1 | 12/2003 | Kordikowski et al. | |
| 2005/0155541 | A1 | 7/2005 | McCausland et al. | |
| 2007/0065372 | A1* | 3/2007 | Price et al. ..................... | 424/46 |

FOREIGN PATENT DOCUMENTS

| DE | 10 2005 011 786 A1 | 9/2006 |
| EP | 1 466 595 A1 | 10/2004 |
| EP | 1782797 A1 | 9/2007 |
| WO | WO-00/35579 A1 | 6/2000 |
| WO | WO-01/74332 A1 | 10/2001 |
| WO | 02089942 | 11/2002 |
| WO | 03105780 | 12/2003 |
| WO | WO-03/101577 A1 | 12/2003 |
| WO | WO-2004/073827 A1 | 9/2004 |
| WO | WO-2005/089375 A2 | 9/2005 |
| WO | WO-2006/056812 A1 | 6/2006 |
| WO | 2007135409 | 11/2007 |
| WO | WO 2008/114052 A1 | 9/2008 |

OTHER PUBLICATIONS

Nagar et. al., Insights into Polymers:Film Formers in Mouth Dissolving Films, Drug Invention Today, 3(12),2011 at p. 282.*
Jones, Harris, Hooton, Shur, King, Mathoulin, Nichol, Smith, Dawson, Ferrie, and Price, "An Investigation into the Relationship Between Carrier-Based Dry Powder Inhalation Performance and Formulation Cohesive-Adhesive Force Balances", European Journal of Pharmaceutics and Biopharmaceutics, 2008, pp. 496-507.
Suslick, Kenneth S., "The Chemical Effects of Ultrasound", Scientific American, Feb. 1989, pp. 80-86.
Suslick, Kenneth S. et al., "Acoustic Cavitation and its Chemical Consequences", Phil. Trans. R. Soc. Lond. A, 1999, vol. 357, pp. 335-353.
Gogate, Parag R. et al., "Cavitation: A technology on the Horizon", Current Science, 2006,vol. 91, No. 1, pp. 35-46.
Begat and Price, "The Influence of Force Control Agents on the Cohesive-Adhesive Balance in Dry Powder Inhaler Formulations" Hosokawa Powder Technology Foundation, No. 23, 2005, pp. 109-121.
Begat, Morton, Staniforth and Price, "The Cohesive-Adhesive Balances in Dry Powder Inhaler Formulations I: Direct Quantification of Atomic Force Microscopy" Pharmaceutical Research, vol. 21, No. 9, 2004, pp. 1591-1597.
Suslick, Didenko, Fang, Hyeon, Kolbeck, McNamara III, Mdleleni and Wong, "Acoustic Cavitation and its Chemical Consequences" Phil. Trans. R. Soc. Lond. A, vol. 357, 1999, pp. 335-353.
Suslick and Doktycz, "Effects of Ultrasound on Surfaces and Solids" Advances in Somochemistry, vol. 1, 1990, pp. 197-230.

* cited by examiner

*Primary Examiner* — Adam C Milligan
(74) *Attorney, Agent, or Firm* — Tarolli, Sundheim, Covell & Tummino LLP

(57) ABSTRACT

This invention provides a process for increasing the crystallinity of at least one solid material which is less than 100% crystalline, comprising contacting said solid material with solvent in which the solid material is insoluble or poorly soluble (a non-solvent); and applying ultrasound to the solid material when in contact with said non-solvent.

6 Claims, 19 Drawing Sheets

Results: Aerosolization Efficiency

|  | % Emitted Fraction (± S.D.) | Fine Particle Dose (± μg) | $FPF_{LD}$ (± %) | MMAD (± GSD) |
| --- | --- | --- | --- | --- |
| Micronized | 85.6 (4.2) | 4.9 (0.9) | 9.7 (0.7) | 4.87 ± 1.97 |
| Sample 2 | 93.7 (3.8) | 7.5 (0.2) | 14.9 (0.6) | 4.48 ± 1.90 |
| Sample 3 | 89.7 (3.7) | 7.8 (0.4) | 15.6 (0.5) | 3.73 ± 2.17 |
| Sample 4 | 90.7 (4.2) | 2.5 (0.3) | 5.1 (0.7) | 4.85 ± 2.08 |

Results: Aerosolization Efficiency Compared to Flixotide

| | % Emitted Fraction (± S.D.) | Fine Particle Dose (± µg) | $FPF_{LD}$ (± %) | MMAD (± GSD) |
|---|---|---|---|---|
| Flixotide | 94.3 (3.4) | 6.1 (0.2) | 12.1 (0.2) | 3.43 ± 2.13 |
| Sample 2 | 93.7 (3.8) | 7.5 (0.2) | 14.9 (0.6) | 4.48 ± 1.90 |
| Sample 3 | 89.7 (3.7) | 7.8 (0.4) | 15.6 (0.5) | 3.73 ± 2.17 |
| Sample 4 | 90.7 (4.2) | 2.5 (0.3) | 5.1 (0.7) | 4.85 ± 2.08 |

|  | Micronised Starting material | | GR005/179/C Pre ultrasonic treatment | | GR005/180/A4 Post ultrasound | |
|---|---|---|---|---|---|---|
| Formulation | 100% (drug only) | 25% | 100% | 25% | 100% | 25% |
| Content [%] |  | 24.2 |  | 25.06 |  | 24.3 |
| RSD [%] |  | 1.7 |  | 3.2 |  | 1.6 |
| FPF [%] | 15.8 | 21.9 | 20.3 | 18.5 | 25.5 | 28.6 |
| RSD [%] | 20.3 | 13.2 | 8.9 | 11.9 | 6.6 | 11.2 |
| FPD [mg] | 4.8 | 1.6 | 6.1 | 1.4 | 7.6 | 2.1 |
| DD [%] | 72.7 | 84.1 | 77.6 | 91.8 | 68.8 | 82.9 |
| RSD [%] | 16.5 | 1.2 | 5.9 | 2.4 | 15.7 | 1.2 |

RSD Relative Standard Deviation; DD Delivered Dose

Fig. 19

|  | Micronised Starting material | | GR005/179/C Pre ultrasonic treatment | | GR005/180/A4 Post ultrasound | |
|---|---|---|---|---|---|---|
| Formulation | 100% | 25% | 100% | 25% | 100% | 25% |
| Content [%] |  | 24.2 |  | 25.06 |  | 24.3 |
| RSD [%] |  | 1.65 |  | 3.2 |  | 1.64 |
| FPF [%] | 3.4 | 15.1 | 5.7 | 15.2 | 7.4 | 21.6 |
| RSD [%] | 14.7 | 13.2 | 26.3 | 3.9 | 10.8 | 3.7 |
| FPD [mg] | 1.0 | 1.1 | 1.7 | 1.1 | 2.3 | 1.6 |
| DD [%] | 93.9 | 88.0 | 93.2 | 91.4 | 93.8 | 89.8 |
| RSD [%] | 2.9 | 3.9 | 3.4 | 3.0 | 1.9 | 3.7 |

RSD Relative Standard Deviation; DD Delivered Dose

Fig. 20

Results: Aerosolization Efficiency – 3 Months

| | FPD (± µg) t = 0 | FPF$_{LD}$ (± %) t = 0 | FPD (± µg) t = 1 m | FPF$_{LD}$ (± %) t = 1m | FPD (± µg) t = 3 m | FPF$_{LD}$ (± %) t = 3m |
|---|---|---|---|---|---|---|
| Micronized | 4.9 (0.9) | 9.7 (0.7) | 2.5 (0.1) | 5.0 (0.2) | 1.6 (0.2) | 3.2 (0.7) |
| Sample 2 | 7.5 (0.2) | 14.9 (0.6) | 6.9 (1.3) | 13.8 (1.8) | 5.4 (1.2) | 10.7 (1.2) |
| Sample 3 | 7.8 (0.4) | 15.6 (0.5) | 7.3 (0.4) | 14.6 (0.6) | 7.6 (0.3) | 15.2 (1.6) |
| Sample 4 | 2.5 (0.3) | 5.1 (0.7) | 1.8 (0.2) | 3.6 (0.3) | 1.9 (0.5) | 3.9 (0.7) |

Results: % Fine Particle Fraction of FP after 1 m storage

|  |  |  | T = 0 | | T = 1 month | |
| --- | --- | --- | --- | --- | --- | --- |
|  |  |  | FPF [%/LD] | SD | FPF [%/LD] | SD |
| FP | Cyclohaler | Micronized | 13.9 | 1.2 | 15.4 | 0.2 |
|  |  | Sample_2 | 16.7 | 1.1 | 17.5 | 0.4 |
|  |  | Sample_3 | 18.9 | 0.8 | 17.2 | 0.8 |
|  |  | Sample_4 | 17.6 | 3.1 | 17.7 | 1.1 |
|  | Rotahaler | Micronized | 14.4 | 2.0 | 14.4 | 0.9 |
|  |  | Sample_2 | 15.5 | 1.7 | 17.5 | 0.6 |
|  |  | Sample_3 | 18.5 | 1.1 | 19.0 | 0.9 |
|  |  | Sample_4 | 5.3 | 0.7 | 8.2 | 1.3 |

PROCESS FOR IMPROVING CRYSTALLINITY

FIELD OF THE INVENTION

The present invention relates to a process for increasing the level of crystallinity and modifying surface characteristics in an amorphous solid material. The present invention has application in the manufacture of chemicals, such as active ingredient compounds and excipients for use in pharmaceutical formulations, such as inhalation formulations, and in the manufacture of agrochemical formulations, such as liquid-based suspensions.

The present invention is also concerned with the production of active drug particles that are to form a dry powder formulation which is to be administered to the lung, for example using a dry powder inhaler (DPI) device. In particular, the present invention provides the characteristics and preferred processing of particles whereby the performance as such is significantly greater than conventional DPI, pressurized metered-dose inhalers (pMDIs) and nasal suspension powders, in particular DPI and pMDI powders, more particularly DPI powders.

BACKGROUND OF THE INVENTION

Two widely used systems for the administration of drugs to the airways are the dry powder inhalers (DPIs) comprising micronized drug particles as dry powder usually admixed with coarser excipient particles of pharmacologically inert materials such as lactose, and the pressurized metered-dose inhalers (pMDIs) which may comprise a suspension of micronized drug particles in a propellant gas. This present invention is relevant to both these methods of delivery.

Nasal delivery is a means to enable administration of drug particles to the central nervous system (CNS—nose to brain), systemic and topical nasal formulations whether as powders or of liquid suspension. Various breath activated devices deliver intranasal drugs to targeted regions of the nasal cavity, including the sinuses and the olfactory region, without lung deposition. This present invention is relevant to this method of delivery.

The control of crystal and precipitate particle size of active and other compositional ingredients is necessary in industries in which the final product form of the active ingredient of interest is in the form of a fine powder, such as in the pharmaceutical and agrochemical industries. The manner in which an active ingredient behaves in a biological system depends upon many factors inter alia the size of the particle and the crystal form. Small particles may be made by processes such as milling, but such processes may have a detrimental effect on the material properties of the milled particles. Furthermore, a significant proportion of particles may be produced which are of a shape that is unsuitable for a given end use. When particles are milled they may undergo morphological alterations, leading to undesirable surface polymorphological transformation which in turn may give rise to the formation of amorphous structures that are unsuitable for end purpose applications, such as in a pharmaceutical formulation designed for inhalation. In addition, milling generates considerable heat which may make particulate milling inappropriate, for example, where the active ingredient is a low melting solid. In addition, the physical performance of particles destined for use in aerosols may be compromised if they become highly charged as a result of milling.

Techniques for the production of drug particles may include the generation of an aerosol of droplets from a solution of the drug and subsequent spray drying of the droplets to solidify the particles. Spray drying is one of the most widely used of industrial processes involving particle formation and drying. It is highly suited for the continuous production of dry solids in either powder, granulate or agglomerate form from, for example, liquid feed stocks as solutions, emulsions or pumpable suspensions. Therefore, spray drying is an ideal process where the end-product should comply with quality standards regarding such parameters as particle size distribution, residual moisture content, bulk density, particle shape and the like. A disadvantage of conventional spray drying techniques is that the particles being dried tend to be in an amorphous form, perhaps as high as 100%, rather than in a crystalline particulate form, since solidification is typically rapid, and in addition the processing leads to a high degree of agglomeration of dried particulates. Freeze drying of aerosol droplets is also used in the art to obtain particles but again, the typically rapid solidification that occurs generally leads to the generation of amorphous particles.

WO 2004/073827 describes the preparation of particles in a process referred to as SAX, comprising the steps of forming a solution of a desired substance in a suitable solvent, generating an aerosol therefrom, collecting the aerosol droplets in a non-solvent for the said substance, and applying ultrasound to the droplets dispersed in the non-solvent to effect crystallisation of the substance. A disadvantage of this technique is the need to have a critical control over the degree of solvent evaporation from the aerosol.

Inhalation represents a very attractive, rapid and patient-friendly route for the delivery of systemically acting drugs, as well as for drugs that are designed to act locally on the lungs themselves, such as asthma, chronic obstructive pulmonary disease and infection. It is particularly desirable and advantageous to develop technologies for delivering drugs to the lungs in a predictable and reproducible manner. Drug inhalation benefits include rapid speed of onset; improved patient acceptance and compliance for a non-invasive systemic route; reduction of side effects; product life cycle extension; improved consistency of delivery; access to new forms of therapy, including higher doses, greater efficiency and accuracy of targeting.

Dry powder inhalation (DPI) plays an important role in the treatment of diseases of the lung. Primarily they were developed to overcome problems encountered using Metered Dose Inhalers (MDIs), and later, because they are propellant free and hence more environmental friendly. Using an MDI the patient has to coordinate inhalation and inhaler actuation so that the aerosol cloud can reach the lungs. Dry Powder Inhalers (DPIs) are breath actuated, so that theoretically the aerosol cloud should reach the lungs without problems. However, problems arise due to technical limitations with respect to handling, content uniformity of dose and control of dose. Also, the inspiratory flow rate varies between patients and depends on the mechanical principle of the DPI. DPIs which reduce the inspiratory flow rate considerably due to a high flow resistance are less suitable, because the rate of lung deposition of an aerosol cloud depends on the inspiratory flow rate.

Powder technology, however, for successful dry powders and DPI products remains a significant technical hurdle. Formulations must have suitable flow properties, not only to assist in the manufacture and metering of the powders, but also to provide reliable and predictable resuspension and fluidisation, and to avoid excessive retention of the powder within the dispensing device. The drug particles or particles of pharmaceutically active material (also referred to herein as API particles) in the resuspended powder must aerosolise appropriately so that they can be transported to the appropriate target area within the lung. Typically, for lung deposition, the active particles have a diameter of less than 10 µm, frequently 0.1 to 7 µm or 0.1 to 5 µm.

In this kind of system the interaction between drug-to-drug and drug-to-carrier particles and particle-to-wall are of great importance for successful drug delivery to the deep lung. The interaction between particles is determined by adhesion forces such as van der Waals, capillary, and coulombic forces. The strength of these forces is affected by the particle size, shape, and morphology. Spherical or rounded particles with a rough surface are considered best for pulmonary drug delivery due to their small contact area and increased separation distance between particles. Large separation distance decreases the attachment forces and improves the powder dispersion. Particle engineering for the optimum drug particles together with DPI device engineering are essential for efficient drug delivery via the lungs. WO 2006056812 reports the invention concerned with a refinement of the processing of particles that are to form a dry powder formulation which is to be administered to the lung using a dry powder inhaler (DPI) device whereby the processing of particles of active material and particles of carrier material is carried out in the presence of additive material to provide a powder composition which exhibits excellent powder properties.

When dry powders are produced in conventional processes, the active particles will vary in size, and often this variation can be considerable. This can make it difficult to ensure that a high enough proportion of the active particles are of the appropriate size for administration to the correct site. It is therefore desirable to have a dry powder formulation wherein the size distribution of the active particles is as narrow as possible. For example, preferably the particle distribution is Gaussian, preferably the particle distribution is monomodal. Further, for example, the geometric standard deviation of the active particle aerodynamic or volumetric size distribution is preferably not more than 2, more preferably not more than 1.8, not more than 1.6, not more than 1.5, not more than 1.4, or even not more than 1.2. This will improve dose efficiency and reproducibility.

The Mass Median Aerodynamic Diameter (MMAD) is the particle diameter below which 50% of the particles enter an impactor suitable for determining in vitro performance of inhaled drug particles and takes account of both shape and density. A sample with a MMAD of (say) 5 µm will have 50 percent of the total mass (i.e. not the total number) of particles with a diameter of more than 5 µm and 50 percent with a diameter of less than 5 µm.

Fine particles, with an MMAD of less than 10 µm and smaller, tend to be increasingly thermodynamically unstable as their surface area to volume ratio increases, which provides an increasing surface free energy with this decreasing particle size, and consequently increases the tendency of particles to agglomerate and the strength of the agglomerate. In the inhaler, agglomeration of fine particles and adherence of such particles to the walls of the inhaler are problems that result in the fine particles leaving the inhaler as large, stable agglomerates, or being unable to leave the inhaler and remaining adhered to the interior of the inhaler, or even clogging or blocking the inhaler.

The uncertainty as to the extent of formation of stable agglomerates of the particles between each actuation of the inhaler, and also between different inhalers and different batches of particles, leads to poor dose reproducibility. Furthermore, the formation of agglomerates means that the MMAD of the active particles can be vastly increased, with agglomerates of the active particles not reaching the required part of the lung. These µm to sub µm particle sizes required for deep lung or systemic delivery lead to the problem that the respirable active particles tend to be highly cohesive, which means they generally exhibit poor flowability and poor aerosolisation.

To overcome the highly cohesive nature of such respirable active particles, formulators have, in the past, included larger carrier particles of an inert excipient in powder formulations, in order to aid both flowability and drug aerosolisation. These large carrier particles have a beneficial effect on the powder formulations because, rather than sticking to one another, the fine active particles tend to adhere to the surfaces of the larger carrier particles whilst in the inhaler device. The active particles are released from the carrier particle surfaces and become dispersed upon actuation of the dispensing device, to give a fine suspension which may be inhaled into the respiratory tract.

Whilst the addition of relatively large carrier particles does tend to improve the powder properties, it also has the effect of diluting the drug, usually to such an extent that 95% or more by total weight of the formulation is carrier. Relatively large amounts of carrier are required in order to have the desired effect on the powder properties because the majority of the fine or ultra-fine active particles need to adhere to the surfaces of the carrier particles, otherwise the cohesive nature of the active particles still dominates the powder and results in poor flowability. The surface area of the carrier particles available for the fine particles to adhere to decreases with increasing diameter of the carrier particles. However, the flow properties tend to become worse with decreasing diameter. Hence, there is a need to find a suitable balance in order to obtain a satisfactory carrier powder. An additional consideration is that one can get segregation if too few carrier particles are included, which is extremely undesirable.

An additional problem experienced by formulators is the variability in surface properties of drug and excipient particles. Each active agent powder has its own unique inherent stickiness or surface energy, which can range tremendously from compound to compound. Further, the nature of the surface energies can change for a given compound depending upon how it is processed. For example, jet milling is notorious for generating significant variations in surface properties because of the aggressive nature of the collisions it employs. Such variations can lead to increased surface energy and increased cohesiveness and adhesiveness. Even in highly regular, crystalline powders, the short range Lifshitz-van der Waals forces can lead to highly cohesive and adhesive powders.

If no carrier excipient is used, the micronized drug particles are loosely agglomerated via Lifshitz-van der Waals forces only. It is important for the function of such a formulation that no capillary forces are formed, because the particle agglomerates must be de-agglomerated in the air stream. Capillary forces are usually several times larger than, for example, Lifshitz-van der Waals forces, and the ability of such an agglomerate to be split into the single particles decreases with increasing autoadhesion forces holding the agglomerates together. Such a loose agglomeration can be achieved using a spheronisation process.

The forces acting on a particle adhered to a carrier particle when placed into an air stream can be described by lift force (the lift of smaller particle away from carrier particle; this can be neglected for micronized powders), the drag force (to compensate for adhesion and friction forces), the adhesion force and friction force (force preventing tangential displacement of two surfaces in contact). These last two hinder the detachment of the drug particles from the carrier surface. The success or failure of an interactive powder mixture as dry powder inhalation depends mainly on the magnitude of the adhesion forces, which fix the drug particles onto the carrier surface.

Obviously, a very high adhesion force is unwanted, because if the drug-carrier units cannot be split into their single components by the drag force, the whole drug-carrier units are swallowed. A balanced adhesion force promotes the split of the drug-carrier units into the micronized drug particles, which are inhaled, and the coarse carrier particles, which are swallowed. On the other hand, a too small adhesion force between drug and carrier particles might result in particle segregation and hence in higher variability in the content uniformity of dose. Also, drug particles are easier removed from the carrier particles during the sliding contact with the inhaler device walls, to which they tend to adhere firmly. Therefore, more drug is lost in the inhaler device.

The prior art teaches that the adhesion force in interactive powder mixtures for inhalation can be manipulated in several ways. First, the carrier particles can be chosen according to their median particle size, shape and surface roughness, which will result in large differences in the adhesion force for a defined mixing procedure and consequently in different aerosolisation properties.

A decrease in median particle size increases the adhesion force between drug and carrier particles. Larger adhesion forces are also found for irregular shaped or elongated carrier particles. This effect can be explained by an increase in friction during mixing. Surface roughness will either increase or decrease the adhesion force depending on the magnitude of the roughness. An increase in adhesion force will be found for extremely smooth carrier particle surfaces due to an increase in the true area of contact, or for very rough carrier particle surfaces, because here the wider spacing between the asperities allows mechanical entrapment of the micronized drug particles.

In typical DPI formulation, powders are pre-blended, which results in autoadhesion between the finer and coarse carrier particles. The finer carrier particles autoadhere, mainly due to mechanical entrapment in the grooves and clefts of the coarse carrier particle surfaces. The amount of finer carrier particles is thus physically removed, and the flow properties of the carrier powder are improved. Corrasion (a geological term implying filling of valleys) leads to a less wavy carrier particle surface, so that micronized drug particles are less likely to be mechanically trapped or embedded in the carrier particle surface. Corrasion also increases the micro-roughness of the carrier particle surfaces and hence reduces the adhesion force between drug and carrier particles due to a reduced true area of contact. However, it has been found that with respect to the adhesion forces and hence the dry powder inhalation function, corrasion is not always of advantage. A minimum surface roughness of the coarse carrier particles is required to allow the embedment of the finer carrier particles in the sense of corrasion. If the coarse carrier particle surface is relatively smooth, the finer carrier particles autoadhere in such a way, that the apparent macro-roughness of the carrier particle surface is increased, which in return offers more sites for the drug particles to be mechanically trapped. In this case, the drug particles can be removed from the carrier particle surfaces only as agglomerates with the finer carrier particles during re-suspension, and the drug deposition in the lungs depends on the size of these agglomerates.

The choice of the carrier material definitely influences the strength of the adhesion forces between drug and carrier particles. However, the place of application i.e. inhalation into the lungs limits this choice dramatically. To date, only lactose monohydrate and glucose are used as carrier materials in commercial dry powder inhalations. Glucose adsorbs moisture rapidly if stored in an environment of more than 55% relative humidity of the storage air. This will lead to strong capillary forces between drug and carrier particles. Lactose monohydrate has been claimed to reduce the vulnerability of the drug-carrier units to increased levels of humidity. However, adhesion force measurements between micronized drug and lactose monohydrate carrier particles after storage under different humidity conditions cast doubts on this opinion.

The use of an interactive powder mixture eases the handling of very low dose drugs for inhalations (for example salmeterol xinafoate: 50 microgram), so that they can be provided in single dose units such as foil blisters (such as in Advair Discus inhaler device) or capsules. Also, the increased homogeneity and reduced segregation of such mixtures is an advantage for the content.

Two common techniques to produce fine particles for DPIs are mechanical micronization and spray drying. A high-energy milling operation generates particles that are highly charged and thus very cohesive. To decrease cohesiveness, surfactants are used, for example, in wet milling. The milling process also introduces surface and crystallographic damage that affects powder stability.

The produced particles often contain irregular fragments that can form strong aggregates. In addition, multistep processing may cause significant losses of materials during powder production and variability of the product properties from batch to batch. Unlike milling, the spray-drying technique is a one-step continuous process that can directly produce pharmaceutical particles with a desired size. No surfactants or other solubilizing agents are needed in the process. However, the thermal history and drying rate of each particle is difficult to control due to the high flow rates needed in the process and limited controllable parameters. Consequently, the produced particles are usually amorphous and thus sensitive to temperature and humidity variations that may cause structural changes and sintering of the particles during storage of the powder.

SUMMARY OF THE INVENTION

According to a first aspect of the invention there is provided a process for increasing the crystallinity of at least one solid material which is less than 100% crystalline, comprising contacting said solid material with solvent in which the solid material is insoluble or poorly soluble; and applying ultrasound to the solid material when in contact with said solvent.

According to a second aspect of the invention, there are provided particles comprising at least one substance obtainable by the process as described herein. There are also provided formulations having particles comprising at least one particulate substance obtainable by the process as described herein.

Such particles and formulations containing them are particularly useful in producing inhalable medicament formulations. Such particles and formulations comprising such particles exhibit surprising in vitro performance compared with conventionally prepared particles. This significant performance increase is quantified by proportional increase in Fine Particle Fraction (FPF, the % relative to the delivered dose, defined as the sum of all stages of an impinger and the throat). These particles have excellent performance characteristics for drug formulation in DPI. These particles also exhibit surprising in vivo performance compared with conventional particles, with respect to rate of dissolution and FPF delivered to the lungs.

Hereinafter, a solvent in which the solid material is insoluble or poorly soluble shall be referred to as a non-solvent. As used herein, a non-solvent is one in which the solid material is soluble in an amount of less than 0.1 mg per ml at 25° C., preferably less than 0.05 mg per ml at 25° C., preferably less than 0.01 mg per ml at 25° C.

Conversely, as used herein, a solvent is one in which the solid material is soluble in an amount of greater than 0.1 mg per ml at 25° C., preferably greater than 0.5 mg per ml at 25° C., preferably greater than 1 mg per ml at 25° C., preferably greater than 5 mg per ml at 25° C., preferably greater than 10 mg per ml at 25° C.

Preferably, the solid material utilised in the present invention is a particulate solid material. The particles preferably have a MMAD of up to about 10 μm, preferably from about 100 nm to about 10 μm, preferably from about 100 nm to about 5 μm and most preferably from about 100 nm to about 2 μm, for example, about 110 nm, about 250 nm, about 400 nm, about 700 nm or about 1 μm, and the like.

The aerodynamic diameter is the diameter of a sphere of unit density which behaves aerodynamically as the particle of the test substance. It is used to compare particles of different sizes, shapes and densities and to predict where in the respiratory tract such particles may be deposited. The term is used in contrast to volume equivalent, optical, measured or geometric diameters which are representations of actual diameters which in themselves cannot be related to deposition within the respiratory tract.

A number of methods are available to determine the size distribution of respirable particles and (to a lesser extent) the distribution of inhalable particles; for an indication of the particle size the Mass Median Aerodynamic Diameter (MMAD) and Geometric Standard Deviation (GSD) can be calculated. The MMAD is a statistically derived figure for a particle sample: for instance, an MMAD of 5 μm means that 50% of the total sample mass will be present in particles having aerodynamic diameters less than 5 μm, and that 50% of the total sample mass will be present in particles having an aerodynamic diameter larger than 5 μm.

Cascade impactors such as the Anderson Cascade Impactor or Next Generation Impactor, preferably Next Generation Impactor, can be used to obtain the size distribution of an aerosol (or a dust cloud). Air samples are withdrawn through a device, which consists of several stages on which particles are deposited on e.g. glass or glass fibre. Particles will impact on a certain stage depending on their size. The cut-off size can be calculated from the jet velocities at each stage by weighing each stage before and after sampling and the MMAD derived from these calculations. Despite the limitations in this method, namely particles bouncing off, overloading and fluctuation in flow rate etc., it is a well established technique to measure the airborne size distribution of an aerosol and it's MMAD.

The particle size can be measured by laser diffraction techniques: Light from a laser is shone into a cloud of particles, which are suspended in a transparent gas such as air. The particles scatter the light; smaller particles scattering the light at larger angles than bigger particles. The scattered light can be measured by a series of photodetectors placed at different angles. This is known as the diffraction pattern for the sample. The diffraction pattern can be used to measure the size of the particles using well documented light scattering theory. The particles are assumed to be spherical but few particles are actually spherical. The particle diameters are calculated from the measured volume of the particle, but assume a sphere of equivalent volume.

Preferably, the solid material utilised in the present invention is obtained from a process selected from the group consisting of mechanical micronization, milling, jet milling, grinding, rapid precipitation, freeze drying, lyophilisation, rapid expansion of supercritical solutions, spray drying or mixtures thereof. Most preferably, the solid material utilised in the present invention is obtained by a process of spray drying. Conventional spray drying techniques may be used. Preferably, the SAX process, such as that disclosed in WO 2004/073827, is not used.

Preferably, prior to the application of one of the above processes, the solid material is substantially amorphous, for example, less than 50% crystalline, more preferably less than 40% crystalline, more preferably less than 25% crystalline, more preferably less than 10% crystalline, more preferably less than 5% crystalline, for example less than 1% crystalline.

When the solid material utilised in the present invention is obtained from mechanical micronization, milling, jet milling, grinding or mixtures thereof, the solid material prior to one of these processes may be substantially crystalline, such as more than 50% crystalline, for example more than 60% crystalline, for example more than 75% crystalline, for example more than 90% crystalline, for example more than 95% crystalline, for example more than 99% crystalline. After one of the four processes, or mixtures thereof, the solid material may be substantially crystalline at the core of the particle, and substantially amorphous on the outer layer of the particle.

A number of techniques may be used to determine crystalline content. For example, PXRD (Powder X-ray Diffraction) is a technique for looking at X-ray Diffraction patterns in solid materials. Crystalline particles have distinct 'finger-print' patterns for a given polymorph. Conversely amorphous compounds show little or no diagnostic patterns and show up simply as a broad hump or noise. Differential Scanning calorimetry (DSC) also reveals a clean melting point and measurement of heat of fusion which can equate to level of crystallinity in a given sample. Amorphous materials show inconsistent behaviour in the DSC profile. DSC of crystalline materials illustrates a sharp endotherm indicating crystalline nature. Dynamic Vapor Sorption (DVS) provides a rapid and continuous method for measuring the isotherm and moisture uptake behaviour of crystalline and amorphous materials. In conjunction with DSC it can be used to measure the stability of products. Finally Raman analysis can give an indication of crystalline material and indeed distinguish between different polymorphs. Amorphous materials do not have the same diagnostic patterns and so are distinguishable from crystalline phases. For the purposes of the present application, Differential Scanning calorimetry (DSC) is the preferred method of measurement of crystallinity. DSC experiments can be performed with a number of commercial apparatus including TA Instruments' DSC Q2000 V24.2 build 107, the latter being the preferred instrument for measuring DCS according to the present invention. Typically an accurate amount of material is charged to the sample pan of the DSC instrument and subjected to a heating ramp of up to 100° C./min to around 275° C. The melting point endotherm and integral of the heat flow, as a measure of heat of fusion, is a qualitative and quantitative measurement respectively of crystallinity. In particular, for a given solid material, DSC provides a direct comparison of two samples thereof and clearly shows whether one is more or less crystalline than the other.

Additionally or alternatively, prior to the application of the present process, the solid material may comprise a metastable crystalline material.

For any particular material, the skilled person can readily determine whether a solid material is insoluble or poorly soluble therein. For example, High Performance Liquid Chromatography (HPLC) or Gas Liquid Chromatography (GLC) allow one to determine the level of solubilised substance in a liquid sample when it is saturated, by analysis of clear samples, making reference against solutions of known concentration. The former method is more typically used for pharmaceutical products whereas the latter is used when the material being analysed is sufficiently volatile to be vaporised at temperatures up to 300° C. which precludes most pharmaceutical products. Preferably, water is used as the non-solvent for poorly water soluble materials. For water soluble materials, preferably non-solvent hydrocarbons are used, for example, heptane. Further non-solvents for water soluble materials may include ethers (methyl tert-buty ether), alcohols (ethanol) and ketones (butanone) as appropriate.

The ultrasound is preferably applied for a suitable period of time and temperature required to convert at least a portion of the amorphous material into crystalline material, or to convert a metastable material into a more stable material. For example, the process is preferably carried out for a period of greater than 0.1 ms, more preferably greater than 1 ms, more preferably greater than 1 minute, for example, between 1 second and 24 hours, more preferably between 1 minute and 6 hours, more preferably between 5 minutes and 1 hour.

Preferably, the solid material used in the present invention is dry. This means that it is preferably substantially free from solvent, including non-solvents, water and organic solvents. This means that the solid material is substantially free of free water or solvent. By substantially free from solvent it is meant that the solid material contains less than 5% by weight of solvent, more preferably less than 4%, more preferably less than 3%, more preferably less than 2%, more preferably less than 1%, more preferably less than 0.5%, more preferably less than 0.1% by weight of solvent.

Solid materials containing water of hydration, and molecular solvates can be substantially free from solvents since they contain only the prerequisite amount of water or solvent necessary for incorporation into the unit cell of the crystal. Otherwise they are essentially free of free water or solvent.

The process of the present invention finds particular utility in the processing of spray dried particles, comprising a substance selected from the group consisting of an active pharmaceutical ingredient, an active agrochemical ingredient, a pharmaceutical excipient, an agrochemical excipient and appropriate mixtures of two or more thereof. By "appropriate", it is meant that active pharmaceutical ingredient may be combined with other active pharmaceutical ingredient and/or pharmaceutical excipient(s), but one would not normally combine a pharmaceutical active ingredient with an agrochemical excipient for example.

In a preferred embodiment of the present invention, there is provided a process for increasing the crystallinity of at least one solid material which is less than 100% crystalline which comprises:

(i) forming a solution of at least one solid material in a solvent;
(ii) subjecting the solution to a process selected from the group consisting of rapid precipitation, freeze drying, lyophilisation, rapid expansion of supercritical solutions, spray drying or mixtures thereof, wherein the said dissolved solid material is converted into a substantially dry solid material;
(iii) optionally isolating the solid material from the liquid and/or gaseous components of the process of step (ii);
(iv) treating said dry solid material from step (ii) or step (iii) with a non-solvent therefor;
(v) applying ultrasound to the solid material from step (iv) when it is in contact with said non-solvent; and
(vi) optionally separating and/or drying the resultant solid material from step (v).

In such a process, step (ii) preferably comprises spray drying of the solution of the solid material. Conventional spray drying may be used. In the spray drying process, the solid material produced is usually substantially amorphous.

Preferably, after the application of step (ii), the material going into step (iii) or (iv) is substantially amorphous, for example, less than 50% crystalline, more preferably less than 40% crystalline, more preferably less than 25% crystalline, more preferably less than 10% crystalline, more preferably less than 5% crystalline, for example less than 1% crystalline.

In step (iv) the term treating means exposing the dry solid material to a non-solvent. This may take place in the same or a separate vessel to the one used to collect the material produced by step (ii). Preferably, the amount of non-solvent is greater than the amount of solid material. For example, the weight ratio of solid material to non-solvent in step (iv) is preferably in the range of 1:100, more preferably 1:10, for example 1:2, 1:3, 1:4, 1:5, etc.

Preferably, the solid material produced by step (ii) and/or step (iii) is substantially dry. This means that preferably all of (100%) of the solid material entering process step (iv) is preferably substantially free from solvent, including water and organic solvents (wherein the term "substantially free from solvent" is defined above).

For any given solid material, the skilled person is capable of determining suitable solvents therefor, without burden. Some examples of solvent suitable for certain solid materials are as follows. Volatile organic solvents such as methanol, ethanol, dichloromethane, ethyl acetate, acetone, 2-propanol and non-organic solvents such as water would be typical solvents for pharmaceutically active ingredients.

Preferred excipients may include, for example, lactose and stearic acid. Lactose may be dissolved in water or ethanol/water mixture. Stearic acid may be dissolved in ethyl acetate or ethanol.

The non-solvent (for example, that in process step (iv)) is preferably substantially free of free water (i.e., water not already bound to the solid material to form a hydrate or the like) when an anhydrous crystal is desired, and also free of any solvent in which the solid material is substantially soluble in. The non-solvent may be water when the solid material is substantially insoluble therein.

Whilst not an exhaustive list, some examples of solvent and non-solvent combinations are shown in Table 1.

TABLE 1

| Solvent (also possible non-solvent) | Non-solvent (also possible solvent) |
|---|---|
| Methanol | Water |
| Acetone | Water |
| Ethanol | Water |
| Ethanol | Cyclohexane |
| Methanol | Cyclohexane |
| Ethanol | 2-Propanol |
| Methanol | 2-Propanol |
| Acetone | Isooctane |
| Ethyl acetate | Heptane |
| Dichloromethane | Heptane |
| Acetone | Heptane |

Other non-solvents suitable for preparing particles of the current invention include hydrofluoroalkane liquids selected from the group consisting of 1,1-difluoroethane, 1,1,1-trifluoroethane, 1,1,1,2-tetrafluoroethane, pentafluoroethane, 1,1,1,3,3-pentafluoropropane, 1,1,1,3,3,3-hexafluoropropane, 1,1,1,2,3,3,3-heptafluoropropane, 1,1,1,3,3-pentafluorobutane and 1,1,1,2,3,4,4,5,5,5-decafluoropentane. Use of such non-solvents can facilitate direct formulation for use in PMDI. In another embodiment less volatile fluorinated compounds such as perfluorodecalin can be used as non-solvent.

The concentration of the solid material (which is preferably a pharmaceutically acceptable substance, a pharmaceutically acceptable excipient or a mixture thereof) in the solution formed in step (i) of the process is preferably from 10 mg/ml to 800 mg/ml, more preferably in the range of 50 mg/ml to 600 mg/ml, more preferably 100 mg/ml to 400 mg/ml.

During the process of the invention, the temperature of the non-solvent preferably lies between −10° C. and +120° C., subject to the non-solvent remaining in liquid form. Preferably, the temperature of the non-solvent preferably lies between 0° C. and 80° C., more preferably 20° C. to 60° C.

Preferably, the above process is sequential, and steps (iv) and (v) take place immediately after step (ii) (or immediately after optional step (iii) where this occurs). By "immediately after", it is preferably meant that the spray dried particles of step (ii) (or step (iii) where it occurs) are processed in steps (iv) and (v) within 1 hour of undergoing step (ii), preferably within 30 minutes, preferably within 5 minutes, preferably within 1 minute of undergoing step (ii). Preferably, "immediately" means without any intermediate steps. Preferably, the above process is a continuous process. For example the process can be continuously fed with unprocessed material, and the processed material can be continuously or incrementally removed. Alternatively, the process may be a batch-type process wherein the process is fed batch-wise with unprocessed material, and the processed material can be removed in batches.

Alternatively, step (ii) and step (iii) can be carried out prior to step (iv), such as 6 months prior, more preferably 3 months prior, more preferably 1 month prior, more preferably 1 week prior, more preferably 1 day prior to step (iv).

The resultant solid material from step (v) may hereinafter be referred to as "active particles".

In a further embodiment of the present invention, there is provided a process for increasing the crystallinity of at least one solid material which is less than 100% crystalline which comprises:

(a) subjecting at least one solid material to mechanical micronization, milling, jet milling, grinding or mixtures thereof;

(b) treating said solid material from step (a) with a non-solvent therefor;

(c) applying ultrasound to the solid material from step (b) when it is in contact with said non-solvent; and (d) optionally separating and/or drying the resultant solid material from step (c).

After the application of step (a), the material going into step (b) is for example more than 50% crystalline, for example more than 60% crystalline, for example more than 75% crystalline, for example more than 90% crystalline, for example more than 95% crystalline, for example more than 99% crystalline, or for example, less than 50% crystalline, for example less than 40% crystalline, for example less than 25% crystalline, for example less than 10% crystalline, for example less than 5% crystalline, for example less than 1% crystalline.

In step (b), the term treating means exposing the dry solid material to a non-solvent. This may take place in the same or a separate vessel to the one used to collect the material produced by step (a). Preferably, the amount of non-solvent is greater than the amount of solid material. For example, the weight ratio of solid material to non-solvent in step (b) is preferably in the range of 1:100, more preferably 1:10, for example 1:2, 1:3, 1:4, 1:5, etc.

Step (b) may occur immediately after step (a) where "immediately after" is as defined above. Alternatively, step (a) can be carried out prior to step (b), such as 6 months prior, preferably 3 months prior, more preferably 1 month prior, more preferably 1 week prior to step (b).

For formulations to reach the deep lung or the blood stream via inhalation, the active agent in the formulation must be in the form of very fine particles, for example, having a mass median aerodynamic diameter (MMAD) of less than 10 μm. It is well established that particles having an MMAD of greater than 10 μm are likely to impact on the walls of the throat and generally do not reach the lung. Particles having an MMAD in the region of 5 to 2 μm will generally be deposited in the respiratory bronchioles whereas particles having an MMAD in the range of 3 to 0.05 μm are likely to be deposited in the alveoli and to be absorbed into the bloodstream.

Ideally the active particles in a dry powder formulation should have an MMAD of not more than 10 μm, preferably not more than 5 μm, more preferably not more than 3 μm, more preferably not more than 2.5 μm, more preferably not more than 2.0 μm, more preferably not more than 1.5 μm, or preferably not more than 1.0 μm.

Of major importance is the composition of a dry powder inhalation. In a dry powder inhaler (DPI), a mixture of active particles (1-5 μm) and coarse carrier particles such as lactose (50-500 μm) may be used to obtain an effective drug particle discharge.

The spray dried particles preferably have a MMAD of up to about 10 μm, preferably from 100 nm to 10 μm, preferably from about 100 nm to about 5 μm and most preferably from 100 nm to about 2 μm, for example, about 110 nm, about 250 nm, about 400 nm, about 700 nm, about 1 μm, and the like.

The final product of the process, the active particles, may also have a MMAD of up to about 10 μm, preferably from 100 nm to 10 μm, preferably from about 100 nm to about 5 μm and most preferably from 100 nm to about 2 μm, for example, about 110 nm, about 250 nm, about 400 nm, about 700 nm, about 1 μm, and the like.

The frequency of the ultrasound waves used in the process of the present invention is preferably in the range of from 16 kHz to 1 MHz, preferably from 10-500 kHz, more preferably from 10-100 kHz such as at 10, at 20, 40, 60, 80, or 100 kHz or at any frequency therebetween.

In addition to increasing the crystallinity of the solid material produced by the process of the present invention, the application of the ultrasound may also be used to reduce the amount of agglomerated particulate material. This agglomeration reduction preferably takes place at the same time as step (v) or (c) referred to above.

Depending on the kind of amorphous, partially amorphous, or metastable crystalline form of the solid material in contact with non-solvent that is subjected to ultrasonic irradiation, the particle may be transformed into a smaller and/or more stable form of itself. For example, an active ingredient may be transformed into a more stable crystalline form or, should the particle prior to ultrasonic irradiation be of a material that is present in an unstable amorphous form, it may be transformed into a more stable amorphous form. Whatever form the particle has when in contact with non-solvent, on application of ultrasonic irradiation as outlined herein, the particle properties are altered, resulting in the formation of more stable particles which may be used in a pharmaceutical or other application, such as an agrochemical application, in a more efficient manner. Preferably, the particles obtained from the process are highly crystalline and stable.

Once the ultrasonic irradiation step has been applied, the isolation of crystals from the particulate slurry may be carried out by any conventional means, such as by filtration, centrifugation, spray-drying, supercritical carbon dioxide extraction, simple evaporation, or mixtures of two or more such techniques. Typically, crystals are isolated using conventional evaporative methods.

By manipulating the spray drying conditions and ultrasonic treatment regime in the process of the present invention the inventors have now made it possible to provide crystals or amorphous bodies having predetermined characteristics. By treating a spray dried material with ultrasound for a predetermined period of time and temperature in a non-solvent, certain characteristics may be reproducibly obtained. These characteristics may include particle morphology, surface free energy, particle size distribution, desired polymorph, and in terms of isolated particles flowability, reduced electrostatic and cohesive/adhesive properties.

The solid material, preferably particulate solid material that is subject to the process of the invention is preferably an active ingredient or a desired precursor thereof, such as a drug or pro-drug or an agrochemical of interest that is able to form crystals or undergo alterations in morphology that results in a more stable form of the particle. Typically, such modified particles possess physical properties that make them more amenable for use in a desired context, such as in conventional drug delivery vehicles or indeed, in drug delivery vehicles that may be designed specifically for at least one given modified particle. As alluded to herein, there may be more than one particle of interest comprised in the initial solution prepared for conventional spray drying (or the initial solution or solid material of any of the other process techniques referred to herein), such as a mixture of two or more particles of interest. In such a context, two or more active ingredients of interest or a combination of at least one pro-drug and at least one drug, or two or more drugs, or two or more agro-chemicals, may be present in the initial solution as solutes or as the initial solid material, depending on the desired end use post ultrasonic treatment. Suitable particles that are able to crystallise under the process conditions of the invention include active ingredients or drugs which can be formed into crystalline particles by the process of the present invention such as corticosteroids, β2-agonists, anticholinergics, leukotriene antagonists, inhalable proteins or peptides, mometasone furoate; beclomethasone dipropionate; budesonide; fluticasone; dexamethasone; flunisolide; triamcinolone; salbutamol; albuterol; terbutaline; salmeterol; bitolterol; ipratropium bromide; oxitropium bromide; sodium cromoglycate; nedocromil sodium; zafirlukast; pranlukast; formoterol; eformoterol; bambuterol; fenoterol; clenbuterol; procaterol; broxaterol; (22R)-6a,9a-difluoro-IIb,21-dihydroxy-16a,17a-propylmethylenedioxy-4-pregnen-3,20-dione; TA-2005; tipredane; insulin; interferons; calcitonins; parathyroid hormones; and granulocyte colony-stimulating factor.

When more than one solid material is used, co-crystals may be formed. Co-crystals can be defined as crystalline complexes of two or more non-identical neutral molecular constituents, such as an active principal or desired precursor thereof, and a guest bound together in the crystal lattice through noncovalent interactions, preferably primarily hydrogen bonding. A guest may be another active principal or desired precursor thereof, or a co-crystal former.

The formation of pharmaceutical co-crystals involves incorporation of a given active pharmaceutical with another pharmaceutically acceptable molecule in the crystal lattice. The resulting multi-component crystalline phase will maintain the intrinsic activity of the parent active pharmaceutical while possessing a distinct physiochemical profile.

As used herein, the term "co-crystal former" denotes one or more additional molecules present in the same crystal structure as the active principal, or desired precursor thereof, which one or more additional molecules are capable of forming a supramolecular synthon with the active principal, or desired precursor thereof, by way of the intermolecular interactions characteristic of the bonding in a co-crystal.

In one embodiment, the co-crystal former comprises one or more molecules having at least one synthon forming moiety selected from the following group: ether, thioether, alcohol, carbonyl, thiol, aldehyde, ketone, thioketone, nitrate ester, phosphate ester, thiophosphate ester, ester, thioester, sulphate ester, carboxylic acid, phosphonic acid, phosphinic acid, sulphonic acid, sulphonamide, amide, primary amine, secondary amine, ammonia, tertiary amine, imine, thiocyanate, cyanamide, oxime, nitrile, diazo, organohalide, nitro, S-containing heterocyclic ring (such as thiophene), N-containing heterocyclic ring (such as pyrrole, imidazole or pyridine), O-containing heterocyclic ring (such as furan, epoxide or peroxide) and hydroxamic acid moieties.

In further embodiments, the guest may be present, for example, in order to form the co-crystal with the active principal or desired precursor thereof. It is contemplated that one or more guests may be included in a co-crystal. Accordingly, the guest is not required to have an activity of its own, although it may have some activity that does not overly derogate from the desired activity of the active agent. A non-active guest may be a compound where no beneficial pharmacological activity has been demonstrated and which are appreciably biologically non-toxic or pharmacologically benign. In some situations, the guest may have the same activity as or an activity complementary to that of the active agent. The guest may be another active principal or desired precursor thereof. For example, some guests may facilitate the therapeutic effect of an active principal or desired precursor thereof. For pharmaceutical formulations, the guest may be any pharmaceutically acceptable molecule(s) that form a co-crystal with the active principal or desired precursor or its salt.

The guest, or co-crystal former, may be an acid and behave in both a neutral manner but with noncovalent interactions (primarily hydrogen bonding), such as in the case of oxalic acid or other suitable carboxylic acids when prepared as a co-crystal with caffeine, and as a proton-donor when in the case of forming ionic salts such as in the reaction or proton-exchange with an amine for example. Similarly benzoic acid and succinic acid behave in a neutral manner (without formal proton exchange) when forming a co-crystal with fluoxetine hydrochloride or in a proton-exchange manner to form ionic salts such as sodium benzoate or sodium succinate. These compounds may be ionic guests in their own right. Neutral guests are preferably nonionic guests. Ionic guests are compounds or complexes having ionic bonding. The guest may be an acid that forms hydrogen bonds with the chloride (or other anion). Ionic guests are compounds or complexes having ionic character, as exemplified by ionic interaction and attraction. The guest may be an acid that forms hydrogen bonds with the pharmaceutical ingredient. For example, suitable guests which are acids include (but not are not limited to): ascorbic acid, glucoheptonic acid, sebacic acid, alginic acid, cyclamic acid, ethane-1,2-disulfonic acid, 2-hydroxyethanesulfonic acid, 2-oxo-5 glutaric acid, naphthalene-1,5-disulfonic acid, nicotinic acid, pyroglutamic acid and 4-acetamidobenzoic acid. The solutes and active principles listed in the specification include the salt and/or solvates thereof. Co-crystals are described in WO2005/089375.

An example of a co-crystal of the present invention is sildenafil, or a pharmaceutically acceptable salt thereof, and acetylsalicylic acid (aspirin).

Other particles which may be made according to the invention include any drug or active ingredient that can be usefully delivered by inhalation, such as, analgesics, e.g. codeine, dihydromorphine, ergotamine, fentanyl or morphine; anginal preparations, e.g. diltiazem; antiallergics, e.g. cromoglycate, ketotifen or nedocromil; anti-infectives, e.g. cephalosporins, penicillins, streptomycin, sulphonamides, tetracyclines or pentamidine; antihistamines, e.g. methapyrilene; anti-inflammatories, e.g. beclomethasone, flunisolide, budesonide, tipredane, triamcinolone acetonide or fluticasone; antitussives, e.g. noscapine; bronchodilators, e.g. ephedrine, adrenaline, fenoterol, formoterol, isoprenaline, metaproterenol, phenylephrine, phenylpropanolamime, pirbuterol, reproterol, rimiterol, salbutamol, salmeterol, terbutalin; isoetharine, tulobuterol, orciprenaline or (−)-4-amino-3,5-dichloro-a[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline; and therapeutic proteins and peptides, e.g. insulin or glucagon. It will be appreciated by the person skilled in the art that where appropriate medicaments comprising active ingredients or drugs may be used in the form of salts (e.g. as alkali metal or amine salts or as acid addition salts) or as esters (e.g. lower alkyl esters) or as solvates (e.g. hydrates) to optimise the activity and/or stability of the medicament.

Particularly suitable medicaments for preparation with particles obtained in accordance with the process of the invention include anti-allergics, bronchodilators and anti-inflammatory steroids of use in the treatment of respiratory disorders such as asthma by inhalation therapy, for example cromoglycate (e.g. as the sodium salt), salbutamol (e.g. as the free base or as the sulphate salt), salmeterol (e.g. as the xinafoate salt), terbutaline (e.g. as the sulphate salt), reproterol (e.g. as the hydrochloride salt), beclomethasone dipropionate (e.g. as the monohydrate), fluticasone propionate, (−)-4-amino-3,5-dichloro-α-[[[6-[2-(2-pyridinyl)ethoxy]hexyl]amino]-methyl]benzenemethanol glycopyrronium bromide, darotropium, aclidinium, tiotropium (e.g. as bromide salt), theophyline, arofylline, zarfirlukast, monterlukast, carmoterol (e.g. as the hydrochloride salt), formoterol (e.g. as the fumarate salt), or indacaterol and physiologically acceptable salts and solvates thereof.

It will again be appreciated by the man skilled in the art that particles made by the process of the invention may contain a combination of two or more active ingredients as alluded to herein. Active ingredients may be selected from suitable combinations of the active ingredients mentioned hereinbefore. Thus, suitable combinations of bronchodilatory agents include ephedrine and theophylline, fenoterol and ipratropium, and isoetharine and phenylephrine.

Further suitable combinations of particles of active ingredients made according to the process of the invention include combinations of corticosteroids, such as budesonide, beclomethasone dipropionate and fluticasone propionate, with β2-agonists, such as salbutamol, terbutaline, salmeterol and formoterol and physiologically acceptable derivatives thereof, especially salts including sulphates.

Further suitable combinations of particles of active ingredients made according to the process of the invention include combinations such as Formoterol and Fluticasone; Beclomethasone and Formoterol; Formoterol and Mometasone; Indacaterol and Mometasone; Ipatropium bromide and Albuterol; Salbutamol and Albuterol; Tiotropium bromide and Formoterol; Glycopyrronium bromide and Indacaterol; Formoterol and Ciclesonide; Beclomethasone/Salmeterol.

In another embodiment three ingredients can be combined including combinations of corticosteroid, bronchodilator (such as a beta agonist), and anticholinergic agent. One example is fluticasone/salmeterol/tiotropium bromide.

Other examples of particles obtainable by the process of the invention may include a cromone which may be sodium cromoglycate or nedocromil, or a carbohydrate, for example, heparin.

The particles made by the process of the invention may comprise an active ingredient suitable for inhalation and may be a pharmacologically active agent for systemic use. For example, such active particles may comprise peptides or polypeptides or proteins such as Deoxyribonuclease (DNase), leukotines or insulin (including pro-insulins), cyclosporin, interleukins, cytokines, anticytokines and cytokine receptors, vaccines, growth hormone, leuprolide and related analogues, intereferons, desmopressin, immunoglobulins, erythropoeitin and calcitonin.

Alternatively, the active ingredient made by the process of the invention may be suitable for oral administration. A drug for oral administration may be one of the systemic drugs mentioned above. The active ingredient may be a substance which exhibits low solubility in the digestive tract, for example, magnesium trisilicate, calcium carbonate and bismuth subnitrate. Organic compounds may include, for example, all products of combinatorial chemistry, rosiglitazone and other related glitazone drugs, hydrochlorothiazide, griseofulvin, lamivudine and other nuclease reverse transcriptase inhibitors, simvastatin and other statin drugs, benzafibrate and other fibrate drugs and loratidine, and any other physiologically tolerable salts and derivatives thereof.

Pharmaceutical excipients suitable for processing according to the present invention include, for example, carbohydrates especially monosaccharides such as fructose, glucose and galactose; non-reducing disaccharides such as sucrose, lactose and trehalose; non-reducing oligosaccharides such as raffinose and melezitose; non reducing starch derived polysaccharides products such as maltodextrins, dextrans and cyclodextrins; and non-reducing alditols such as mannitol and xylitol. Further suitable excipients include cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). Mixtures of two or more of any of the above excipients are also envisaged.

For use in medicine, the salts of the compounds of this invention refer to non toxic "pharmaceutically acceptable salts." FDA approved pharmaceutical acceptable salt forms (International J. Pharm. 1986, 33,201 217; J. Pharm. Sci., 1977, January, 66 (1), p1) include pharmaceutically acceptable acidic/anionic or basic/cationic salts.

Pharmaceutically acceptable salts of the acidic or basic compounds of the invention can of course be made by conventional procedures, such as by reacting the free base or acid with at least a stoichiometric amount of the desired salt forming acid or base.

Pharmaceutically acceptable salts of the acidic compounds of the invention include salts with inorganic cations such as sodium, potassium, calcium, magnesium, zinc, and ammonium, and salts with organic bases. Suitable organic bases include N methyl D glucamine, arginine, benzathine, diolamine, olamine, procaine and tromethamine.

Pharmaceutically acceptable salts of the basic compounds of the invention include salts derived from organic or inorganic acids. Suitable anions include acetate, adipate, besylate, bromide, camsylate, chloride, citrate, edisylate, estolate, fumarate, gluceptate, gluconate, glucuronate, hippurate, hyclate, hydrobromide, hydrochloride, iodide, isethionate, lactate, lactobionate, maleate, mesylate, methylbromide, methylsulfate, napsylate, nitrate, oleate, pamoate, phosphate, polygalacturonate, stearate, succinate, sulfate, sulfosalicylate, tannate, tartrate, terephthalate, tosylate and triethiodide.

Where the particles of active ingredient(s) prepared by the process of the present invention are agrochemically active, the active ingredient may for example be a plant growth regulator, herbicide, and/or pesticide, for example insecticide, fungicide, acaricide, nematocide, miticide, rodenticide, bactericide, molluscicide or bird repellant.

Examples of organic water-insoluble agrochemical active ingredients made according to the process of the invention include insecticides, for example selected from the group consisting of carbamates, such as methomyl, carbaryl, carbofuran, or aldicarb; organo thiophosphates such as EPN, isofenphos, isoxathion, chlorpyrifos, or chlormephos; organo phosphates such as terbufos, monocrotophos, or terachlorvinphos; perchlorinated organics such as methoxychlor; synthetic pyrethroids such as fenvalerate; nematicide carbamates, such as oxamyl herbicides, for example selected from the group consisting of triazines such as metribuzin, hexaxinone, or atrazine; sulfonylureas such as 2-chloro-N-[(4-methoxy-6-methyl-I,3,5-triazin-2-yl)aminocarbonyl]-benzenesulfonamide; uracils (pyrimidines) such as lenacil, bromacil, or terbacil; ureas such as linuron, diuron, siduron, or neburon; acetanilides such as alachlor, or metolachlor; thiocarbamates such as benthiocarb (SATURN), triallate; oxadiazol-ones such as oxadiazon; phenoxyacetic acids such as 2,4-D; diphenyl ethers such as fluazifop-butyl, acifluorfen, bifenox, or oxyfluorfen; dinitro anilines such as trifluralin; glycine phosphonates such as glyphosate salts and esters; dihalobenzonitriles such as bromoxynil, or ioxynil; fungicides, for example selected from the group consisting of nitrilo oximes such as cymoxanil (curzate); imidazoles such as benomyl, carbendazim, or thiophanate-methyl; triazoles such as triadimefon; sulfenamides such as captan; dithiocarbamates such as maneb, mancozeb, or thiram; chloronated aromatics such as chloroneb; dichloro anilines such as iprodione; aphicides, for example selected in the group consisting of carbamates, such as pirimicarb; miticides, for example selected from the group consisting of propynyl sulfites such as propargite; triazapentadienes such as amitraz; chlorinated aromatics such as chlorobenzilate, or tetradifan; and dinitrophenols such as binapacryl.

The organic water-insoluble agrochemical active ingredients may be comprised in the particles produced according to the present invention as a mixture of several ingredients. Especially preferred organic water-insoluble agrochemical active ingredients are atrazine, cymoxanil, chlorothalnil, cyproconazole, and tebuconazole.

It will be appreciated that the non-solvent and the solvent should be selected as being suitable for a particular active ingredient or active precursor thereof. Corticosteroids, such as budesonide, beclomethasone dipropionate and fluticasone propionate may be dissolved in dichlormethane or methanol and ultrasonically treated in non-solvents such as heptane. β2-agonists, such as salmeterol xinafoate and formoterol fumarate, may be dissolved in methanol and ultrasonically treated in non-solvents such as acetone, ethyl acetate or heptane.

Following a conventional separation step, such as cyclonic separation, the dried particle is placed in contact with a non-solvent and then subjected to ultrasonic irradiation to form crystals, or to anneal and/or stabilise amorphous structures of a desired MMAD as hereinbefore described. The particles are subject to the operating vicinity of the ultrasonic probe if used, or of an ultrasonic energy transducer, such as a wrap-around ultrasonic energy transducer assembly, if such a configuration is employed. A suitable example of such a device is documented in WO 00/35579. The ultrasonic energy may be applied continuously or in a discontinuous manner, such as by pulsed application. Any suitable source of ultrasonic irradiation may be used. An ultrasonic probe may, for example, be inserted into a mixing vessel, such as a continuous ultrasonic flow cell, an ultrasonic emitter may be contained in the mixing vessel, or the mixing vessel may be housed in an ultrasonic bath or it may have an ultrasound transducer fixed to the external walls of the mixing vessel. The amplitude and frequency of the ultrasound waves affects the rate of nucleation and crystal growth. The frequency of the ultrasound waves may for example be from 16 kHz to 1 MHz, preferably from 10-500 kHz, more preferably from 10-100 kHz such as at 10, at 20, 40, 60, 80, or 100 kHz or at any frequency therebetween, such as, 30 kHz or 50 kHz.

The ultrasonic irradiation is employed at an amplitude or power density that is appropriate for the production of crystals of the desired size, for a pre-determined application. For laboratory probe systems with an emitting face of, for example 80 $cm^2$, the amplitude selected may be from about 1-30 μm, typically from 3-20 μm, preferably from 5-10 μm, for example, 6 μm. Probes having a probe face surface area of 8 $cm^2$ and a power requirement of from 5-80 W, provide a power density of from about 0.6-12.5 $W/cm^2$ using an amplitude of 2-15 μm. In larger systems, preferably such as those embodied in WO 03/101577, comprising transducers bonded onto the flow cell, for example a 6 liter flow cell, the power density for the transducers employed may be from 10-100 W/L, preferably from 30-80 W/L, and more preferably from 50-75 W/L, for example 60 W/L or 70 W/L. The present invention is particularly suitable for industrial scale production.

The residence time of the mixed components in the ultrasonic flow cell may be preferably greater than 0.1 ms, more preferably greater than 1 ms, more preferably greater than 1 minute, for example between 1 second and 24 hours, more preferably between 1 minute and 6 hours, more preferably between 5 minutes and 1 hour.

Generated crystals may be gathered or harvested from the batch chamber by drawing off crystals using conventional means in the art, or as an aqueous suspension.

The particles produced according to the invention are substantially crystalline and show a reduced tendency of moisture adsorption which contributes to increase their physical and chemical stability. "Substantially crystalline" means the degree of crystallinity of the particles, expressed as weight % of the crystalline particle with respect to the total weight of the particle, is greater than 90%, preferably greater than 93%, even more preferably greater than 95%. Said particles also exhibit excellent dispersion properties allowing to easily obtaining homogenous formulations, in particular when the particles are formulated as dry powders for inhalation. The degree of crystallinity of the particle may be determined using Differential Scanning calorimetry (DSC), X-ray powder diffraction or other techniques known to the skilled person such as microcalorimetry, preferably DSC.

In one embodiment the solid material is a corticosteroid and preferably is any corticosteroid insoluble or poorly-soluble in water according to the definition of solubility given in the European Pharmacopoeia Ed. $4^{th}$, 2002, which can be utilised by inhalation for the prevention and/or treatment of respiratory diseases. Preferably the corticosteriod has a single therapeutical dose higher than 50 µg, preferably equal to or higher than 80 µg, more preferably equal to higher than 100 µg.

Preferably, the corticosteroid is selected from the group consisting of beclomethasone dipropionate (BDP), budesonide, ciclesonide, mometasone and esters thereof, such as furoate, and fluticasone and esters thereof, such as propionate and furoate. In a preferred embodiment of the invention the corticosteroid is budesonide or fluticasone and salts or esters thereof.

Preferably the active particles of the invention have a volume diameter of less than 10 µm, more preferably at least 90 wt % of the active ingredient particles in a given composition have a diameter equal to or lower than 10 µm as determined by measuring the characteristic equivalent sphere diameter, known as volume diameter, by laser diffraction as described above, preferably using a Malvern or equivalent apparatus. The parameters taken into consideration are the volume diameters (VD) in microns of 10%, 50% and 90% of the particles expressed as d(10), d(50) and d(90), respectively, which correspond to the mass diameter assuming a size independent density for the particles.

Preferably no more than 10 wt % of said particles have a volume diameter d(10) lower than 0.8 µm, preferably no more than 50 wt % of said particles have a volume diameter d(50) lower than 2.0 µm, preferably at least 90 wt % of said particles have a volume diameter d(90) equal to or lower than 10 µm. Preferably 100 wt % of said particles have a volume diameter equal to or lower than 10 µm.

The active ingredients in the particles of the invention are substantially in a pure form. "Substantially in a pure form" means at least 95% w/w pure, preferably at least 98% or at least 99% w/w. The chemical purity may be determined according to methods known to the skilled person such as high-performance liquid chromatography (HPLC).

In another aspect the present invention provides a formulation for administration by inhalation comprising the particles of the invention. The particles may be formulated into said formulation together with one or more pharmaceutically acceptable excipients, additives, diluents or carriers. For example, the formulation is provided in the form of suspension in a propellant as aerosol carrier to be administered by pressurized metered dose inhalers (pMDI).

The suspension formulation may comprise additional excipients such as surfactant, and wetting agent.

In a preferred embodiment, the formulation is provided in the form of dry inhalation powder, more preferably in the form of interactive ordered mixtures, i.e. by diluting the particles of the invention in a pharmacologically inert physiologically acceptable excipient consisting of coarser particles.

Advantageously, said powder formulation for inhalation may comprise the particles according to the invention and coarse particles of a physiologically acceptable excipient, hereinafter "carrier particles", e.g. particles having a mass median particle diameter (MMD) higher than 50 µm and preferably the MMD comprised between 50 µm and 500 µm, more preferably between 150 and 400 µm, even more preferably between 210 and 355 µm. In another embodiment, the coarse particles have a MMD comprised between 90 and 150 µm. The MMD is the particle diameter that divides the frequency distribution in half; fifty percent of the aerosol mass has particles with a larger diameter, and fifty percent of the aerosol mass has particles with a smaller diameter.

Preferably at least 50% by weight of the carrier particles have a diameter of less than 500 µm, more preferably at least 80% by weight of the carrier particles have a diameter of less than 500 µm, more preferably at least 90% by weight of the carrier particles have a diameter of less than 500 µm, more preferably 100% by weight of the carrier particles have a diameter of less than 500 µm.

The physiologically acceptable excipient may be constituted of any amorphous or crystalline physiologically acceptable pharmacologically-inert material of animal or vegetable source or combination thereof. Preferred materials are crystalline sugars and for example monosaccharides such as glucose or arabinose, or disaccharides such as maltose, saccharose, dextrose or lactose. Polyalcohols such as mannitol, sorbitol, maltitol, lactitol may also be used. The most preferred material is α-lactose monohydrate.

Examples of commercial lactose are Capsulac™ and Pharmatose™. An example of commercial mannitol is Pearlitol™.

The formulation may be provided in the form of a suspension or a powder to be administered by breath activated nasal inhalers.

Said powder formulation may be administered by inhalation with any type of DPIs known in the art.

DPIs can be divided into two basic types: i) single dose inhalers, for the administration of pre-subdivided single doses of the active compound; ii) multidose dry powder inhalers (MDPIs), either with pre-subdivided single doses or pre-loaded with quantities of active ingredient sufficient for multiple doses. On the basis of the required inspiratory flow rates (l/min) which in turn are strictly depending on their design and mechanical features, DPIs are divided in: i) low-resistance devices (>90 l/min); ii) medium-resistance devices (about 60 l/min); iii) high-resistance devices (about 30 l/min).

Having regard to the pharmacological activity of the active ingredients, the particles of the invention may be indicated for the prevention and/or treatment of mild, moderate or severe acute or chronic symptoms or for prophylactic treatment of respiratory diseases such as asthma and chronic obstructive pulmonary disease (COPD). Other respiratory disorders characterized by obstruction of the peripheral airways as a result of inflammation and presence of mucus such as chronic obstructive bronchiolitis and chronic bronchitis may also benefit by their use.

For administration via inhalation, the particulate active ingredients produced according to the present process are preferably formulated with carrier particles. Said active ingredient may be present in 0.1%-90% by weight of the formulation, preferably 0.25%-50%, more preferably 1-25% by weight of the formulation. Preferably, the carrier particles may be present in an amount of 10-99.9% by weight of the formulation, more preferably 50%-99.75%, more preferably 75-99% by weight of the formulation.

In a particularly preferred embodiment, the active ingredient in the particle produced according to the present invention comprises (preferably consists essentially of) fluticasone propionate, budesonide, formoterol, salmeterol, beclomethasone or betamethasone, and mixtures and co-crystals thereof. This list also encompasses salts, hydrates and solvates of said compounds.

By scanning electron microscopy (SEM), it can be clearly observed that said active particles are significantly distinct when compared to the SEM image of the starting materials. It can also be appreciated that the particles of the invention exhibit a more uniform and regular spheroidal shape and do not appear to be as fractured and irregular as the starting materials with a smaller amount of fine particles being also present. Without being limited by the theory, said difference in the surface morphology is believed to contribute to explain the lower tendency of aggregation of the particles of invention, and hence their excellent dispersion properties.

Particles of active ingredient produced according to the present invention are preferably substantially spheroidal. This does not preclude particles with roughened surfaces. Preferably, the particles produced according to the present invention have an average ratio of their largest diameter to their smallest diameter of 1.3-1:1, more preferably 1.25-1:1, more preferably, 1.2-1.01:1, more preferably 1.15-1.02:1, more preferably, 1.1-1.03:1, more preferably, 1.075-1.05:1. Thus, it can be seen that the particles of the present invention are substantially spheroidal.

A number of particles size and shape analysis instruments are available such as the Sympatec QICPIC image analysis sensor, which combines particle size and shape analysis. This technique with extremely short exposure time of less than 1 ns allows for the use of dispersion units to provide clear images also from fastest particles with a speed of up to 100 m/s. This guarantees proper dispersion of agglomerated fine and cohesive powders. Particle sizes of between 1 μm and 20 μm can measured. The primary measurement data is stored in 30000 primary classes and can be evaluated in individually definable formats. Pre-defined set of size classes allow an easy adoption to existing measurement specifications. A high performance data compression module supports the acquisition of up to 500 images per second. Particles of less than 1 μm can be measured by laser diffraction techniques such as Malvern or Sympactec diffraction as described earlier, preferably Malvern laser diffraction.

It is well known that the force required to aerosolise an adhered API drug particle is directly proportional to the sum of the surface energies of the contiguous surfaces, and inversely proportional to the projected contact area. Thus the most common approaches to improve the aerosolisation efficiency in DPI is to reduce the surface free energy of the contacting surfaces or modify the particle shape to limit contact area. Surface area is not solely determined by particle size and shape; the surface morphology also contributes to surface area: corrugated (i.e. rough) particles have more surface area than smooth particles that occupy the same volume.

Drug particles prepared by the method of this invention can be defined by specific surface morphology. The inter-particulate forces can be modulated to enhance lung deposition. Ideally, the contact area and thus the forces should be adjusted to a level that provides enough adhesion between drug and carrier to provide a stable formulation, yet allows easy separation upon inhalation. The influence of surface corrugation on the fine-particle fraction can be clarified.

Smooth-surface lactose carrier particles have been shown to increase the fine-particle fraction and dispersibility of micronized drug, while other studies showed that corrugated carrier particles increased the fine-particle fraction. These apparently contradictory results can be explained by the postulate that the surface force balance depends on several variables, not simply surface structure.

For particles described by way of example, surface area and morphology measurements reveal that surface area is highly correlated with particle interactions. Determining the powder surface area involves measuring the volume of gas adsorbed to the powder surface at a given pressure. Over the last few decades, new techniques for studying surfaces have emerged.

The surface area of the particles of the present invention was determined by the Accelerated Surface Area and Porosimetry Analyser (model ASAP 2000, Micromeritics, Norcross, Ga.) using nitrogen as the adsorbate gas. The powder materials (0.3-0.7 g) were degassed for approximately 24 h under nitrogen at 45° C. to remove the preadsorbed gases and vapors from the surface of the samples. The surface area was determined by the multipoint Brunauer, Emmett and Teller (BET) method using the adsorption data in the relative pressure (P/Po) range of 0.07-0.22.

Preferably the particles of this invention will have a surface area in the range 6-22 $m^2/g$, preferably 9-18 $m^2/g$, more preferably 10-13 $m^2/g$, more preferably about 12 $m^2/g$.

Inverse Gas Chromatography (IGC) is a gas-phase technique for characterising surface and bulk properties of solid materials. The principles of IGC are very simple, being the reverse of a conventional gas chromatographic (GC) experiment. A cylindrical column is uniformly packed with the solid material of interest, typically a powder, fibre or film and the retention time and elution peak shape are studied for a series of well-characterized nonpolar and polar gases. A pulse or constant concentration of gas is injected down the column at a fixed carrier gas flow rate, and the time taken for the pulse or concentration front to elute down the column is measured by a detector. A series of IGC measurements with different gas phase probe molecules then allows access to a wide range. IGC is used to measure surface energy as well as to study small changes in surface characteristics caused by processing.

IGC was used to measure surface energy of the particles of this invention. IGC can be carried out with two sets of conditions. At finite dilution the adsorption isotherms can be derived from peak profiles and used to calculate adsorption energy distributions. Secondly at infinite dilution amounts of solute close to the detection limit of the instrument are injected and in this case the solute-solute interactions are small and only solute-sorbent interactions influence the measured retention time. This can yield both dispersive and specific interaction between probe (gas) molecule and stationary powder. The particles of the invention are characterised by having isoenergetic distribution of surface energy as shown quite clearly in FIG. 21. The surface energy is very similar and near identical at both finite and infinite dilution for particles prepared by the preferred method of this inventions, whereas typical micronized particles show dramatic variances at finite and infinite dilution.

Atomic force microscopy (AFM) can be used to measure the cohesive-adhesive balance and works by measuring height, with the probing tip placed in contact with the surface of the sample (contact mode atomic force microscopy) or very close to the surface of the sample (noncontact and tapping mode atomic force microscopy). The probing tip is attached to an elastic cantilever that is deflected proportionally to the force experienced by the tip. The atomic force microscope raster-scans the sample, producing a matrix of data points, from which quantitative height and roughness measurements can be extracted. Tapping mode atomic force microscopy effectively images crystals of various organic compounds, including drugs and the adhesional properties of carrier-particle lactose. Colloid probe microscopy (CPM) is routinely used to measure particle-particle adhesion between microcrystalline particles.

The degree of corrugation and surface morphology of samples was quantified using AFM. The surface topography and roughness measurements of particles of this invention were investigated using a Nanoscope IIIa controller, a Multimode AFM and a J-type scanner (all DI, Santa Babara, Calif., USA). All AFM surface topography images were recorded in Tapping Mode operation, in which, imaging was conducted using TESP Olympus tips (Di, Cambridge, UK) at a scan rate of 1 Hz. Surface roughness measurements were analysed over a 1 μm×1 μm area. To quantify the variations in the surface properties of the crystal surfaces, the root-mean-squared surface roughness measurement ($R_q$) and the mean surface roughness ($R_a$) of the height deviations of the surface asperities were computed.

Prior to force measurements, particles for each batch of sample were attached onto standard V-shaped tipless cantilevers with pre-defined spring constants (DNP-020, DI, CA, USA) using an epoxy resin glue (Araldite, Cambridge, UK). Three tips were prepared for each sample, and all probes were examined with an optical microscope (magnification 50×) to ensure the integrity of the attached particle, before allowing the thin layer of glue to dry.

The substrate was loaded on to the AFM scanner stage, which was enclosed in a custom-built environmental chamber, in which the ambient conditions were maintained at a constant temperature of 25° C. (±1.5° C.) and relative humidity of 35% RH (±3%). The interaction forces were measured by recording the deflection of the AFM cantilever as a function of the substrate displacement (z) by applying Hooke's Law ($F=-kz$). Individual force curves (n=1024) were conducted over a 10 μm×10 μm area at a scan rate of 4 Hz and a compressive load of 40 nN. Parameters were kept constant.

The particles of the invention are characterised by having substantially corrugated surfaces as shown in FIG. 22. Preferably, particles of the present invention have nanometer scale surface corrugations. Preferably the value of $R_q$ is between 10 and 100 nm, more preferably between 20 and 90 nm. Preferably the value of $R_a$ is between 10 and 100 nm, more preferably between 20 and 90 nm.

The cohesive-adhesive balance (CAB) approach of the AFM colloid probe technique is a development that enables direct quantification of the cohesive and adhesive nature—"the force balance" of an API within a formulation. It is a commercially available screening tool in determining the cohesive/adhesive force interactions between potential formulation components using milligrams or less of material.

The CAB approach measures the forces of interaction between API particles, mounted as colloid AFM probes, and well-defined crystalline surfaces of the API and carrier substrates. A CAB plot generated from the interaction of a number of probes allows a characteristic measurement of the cohesive nature of the API, in relation to its adhesive propensity with an excipient material to be quantified. The development of the CAB approach has overcome a number of the limitations associated with conventional AFM colloid probe methodologies, including issues regarding instrumental validation and the need to determine the true area of contact of the interacting surfaces. A CAB value of 1 indicates that the forces of particle-carrier adhesion equals the forces of particle-particle cohesion. A CAB ratio <1 indicates that, all other variables being equal, the drug is more adhesive to the carrier than cohesive with itself, and so might be expected to form a stable, ordered mixture upon blending. A CAB ratio >1, however, indicates that the drug is more cohesive with itself than adhesive to the carrier, suggesting that upon blending a less uniform mixture might be produced, containing agglomerates of drug. Drug-carrier combinations with a higher CAB ratio, such as >1, results in a higher fine particle fraction (FPF) upon aerosolisation, despite potential difference between the carriers in terms of size, shape, roughness and flowability. Drug-carrier combinations with a lower CAB ratio, such as, <1 result in greater cohesion of the active particle to the carrier, therefore the active particle is more likely to remain attached to the carrier. This means that in an inhaled composition, the active particle which remains attached to the carrier particle may not reach the lung and may be deposited in the throat or on the tongue. Preferably, the particles produced according to the present invention have much lower cohesiveness than particles prepared by other methods including micronization and milling. With respect to a measure of cohesiveness, since all substrates will be different with respect to their cohesive and adhesive properties, the CAB ratio is a dimensionless value which is a more useful measure for comparison. Preferably, the particles produced according to the present invention have CAB ratios with the carrier particles of 0.8-1.3, more preferably 0.9-1.2, more preferably, 1.0-1.1. This is a careful balance between the cohesion of the drug with itself and the adhesion of the drug with the carrier.

The chemical and physical stability and the pharmaceutical acceptability of the aerosol formulations according to the invention may be determined by techniques well known to those skilled in the art. Thus, for example, the chemical stability of the components may be determined by HPLC assay, for example, after prolonged storage of the product. Physical stability data may be gained from other conventional analytical techniques such as, for example, by leak testing, by valve delivery assay (average shot weights per actuation), by dose reproducibility assay (active ingredient per actuation) and spray distribution analysis.

The particle size distribution of the aerosol formulations according to the invention may be measured by conventional techniques, for example by using a Next Generation Impactor (NGI) with pre-separator for example by cascade impaction or by the "Twin Impinger" analytical process. As used herein reference to the "Twin Impinger" assay means "Determination of the deposition of the emitted dose in pressurised inhalations using apparatus A" as defined in British Pharmacopoeia 1988, pages A204-207, Appendix XVII C. Such methods involve filling the pre-separator with HPLC mobile phase and the cups of the NGI cups were coated with 1% v/v silicone oil in hexane to eliminate particle bounce. Typically four individual capsules of the same formulation are discharged into the NGI under prescribed conditions. Following aerosolization, the NGI apparatus is dismantled and the inhaler, capsules and each part of the NGI washed down into known volumes of HPLC mobile phase. The mass of drug deposited on each part of the NGI can then be determined by HPLC. The FPD determined represents the mass of drug collected on stages 3-8 of the NGI. The FPF emitted dose is also determined. The aerosolisation efficiency as determined by percentage fine particle fraction (% FPF) or respirable fraction is also assessed.

Such techniques enable the "respirable fraction" of the aerosol formulations to be calculated. As used herein reference to "respirable fraction" means the amount of active ingredient collected in the lower chamber in the NGI per actuation expressed as a percentage of the total amount of active ingredient delivered per actuation using the method described above. The formulations according to the invention have been found to have a respirable fraction of 10-30% or more by weight of the emitted dose of the medicament, preferably 14-26%, for example about 15.9% and about 25.9% as exemplified by examples 2 and 3 (shown in FIGS. 13 and 19). For example 1 (budesonide), example 2 (fluticasone propionate) and example 8 (fenoterol hydrobromide) there was a 53%, 50-60% and 30-50% respectively increase in FPF for the particles of the present invention compared to the prior art.

The propellants for use in the inhalable formulations including particles according to the present invention comprise any fluorocarbon or hydrogen-containing chlorofluorocarbon or mixtures thereof having a sufficient vapour pressure to render them effective as propellants. Preferably the propellant will be a non-solvent for the medicament. Suitable propellants include conventional hydrogen-containing chlorofluorocarbons, non-chlorofluorocarbons, hydrogen-containing fluorocarbons and perfluorocarbons, and the like. In particular the propellants HFA 134a, and HFA 227 or mixtures thereof may be advantageously used.

The formulations according to the invention may be filled into canisters suitable for delivering pharmaceutical aerosol formulations. Canisters generally comprise a container capable of withstanding the vapour pressure of the propellant used such as a plastic or plastic-coated glass bottle or preferably a metal can, for example an aluminium can which may optionally be anodised, lacquer-coated and/or plastic-coated, which container is closed with a metering valve. The metering valves are designed to deliver a metered amount of the formulation per actuation and incorporate a gasket to prevent leakage of propellant through the valve. The gasket may comprise any suitable elastomeric material such as for example low density polyethylene, chlorobutyl, black and white butadiene-acrylonitrile rubbers, butyl rubber and neoprene.

Suitable valves are commercially available from manufacturers well known in the aerosol industry, for example, from Valois, France (e.g. DF10, DF30, DF60), Bespak plc, UK (e.g. BK300, BK356) and 3M-Neotechnic Ltd, UK (e.g. SpraymiserW).

Conventional bulk manufacturing methods and machinery well known to those skilled in the art of pharmaceutical aerosol manufacture may be employed for the preparation of large scale batches for the commercial production of filled canisters.

Typically, in batches prepared for pharmaceutical use, each filled canister is check weighed, coded with a batch number and packed into a tray for storage before release testing.

Each filled canister is conveniently fitted into a suitable channelling device prior to use to form a metered dose inhaler for administration of the medicament into the lungs or nasal cavity of a patient. Suitable channelling devices comprise for example a valve actuator and a cylindrical or cone-like passage through which medicament may be delivered from the filled canister via the metering valve to the nose or mouth of a patient e.g. a mouthpiece actuator. Metered dose inhalers are designed to deliver a fixed unit dosage of medicament per actuation or "puff", for example in the range of 10 to 5000 microgram medicament per puff. Administration of medicament may be indicated for the treatment of mild, moderate or severe acute or chronic symptoms or for prophylactic treatment. It will be appreciated that the precise dose administered will depend on the age and condition of the patient, the particular particulate medicament used and the frequency of administration and will ultimately be at the discretion of the attendant physician. When combinations of medicaments are employed the dose of each component of the combination will in general be that employed for each component when used alone. Typically, administration may be one or more times, for example from 1 to 8 times per day, giving for example 1, 2, 3 or 4 puffs each time.

Suitable daily doses, may be, for example in the range 50 to 200 µg of salmeterol, 100 to 1000 µg of salbutamol, 50 to 2000 µg of fluticasone propionate or 100 to 2000 µg of beclomethasone dipropionate, depending on the severity of the disease.

Thus, for example, each valve actuation may deliver 25 µg salmeterol, 100 µg salbutamol, 25, 50, 125 or 250 µg fluticasone propionate or 50, 100, 200 or 250 µg beclomethasone dipropionate. Typically each filled canister for use in a metered dose inhaler contains 100, 160 or 240 metered doses or puffs of medicament.

The filled canisters and metered dose inhalers described herein comprise further aspects of the present invention.

The invention will now be described with reference to the accompanying examples and figures. It is to be understood that the examples and figures are not to be construed as limiting the scope of the invention in any manner.

BRIEF DESCRIPTION OF THE DRAWINGS

The process of the invention may be carried out using conventional equipment as shown in the accompanying figures in which:

FIG. 13 shows aerosol efficiency of various samples.

FIG. 14 shows bar chart representation of Fine Particle Fraction.

FIG. 15 shows aerosol efficiency compared with GSK's Flixotide.

FIG. 16 Particles of Fenoterol hydrobromide post ultrasonic treatment.

FIG. 19 Comparative Fine Particle Fraction (FPF) data using inhalation device.

FIG. 20 Comparative Fine Particle Fraction (FPF) data using inhalation proprietary test rig.

FIG. 23 shows aerosol efficiency of various samples of FP following 1 and 3 months storage.

FIG. 24 shows a bar chart comparing the aerosol efficiency of various samples of FP following 1 and 3 months storage.

DETAILED DESCRIPTION OF THE INVENTION

Figure 1:
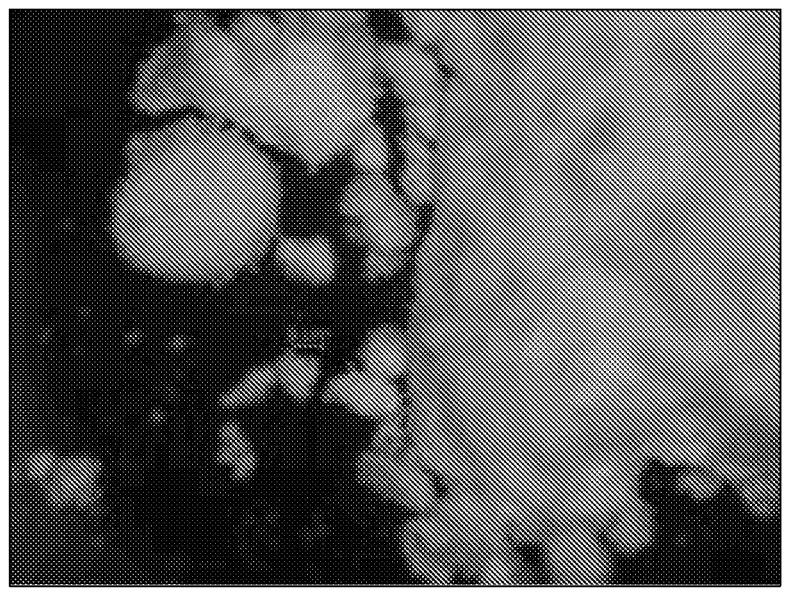
FIG. 1 shows conventionally spray dried budesonide (with ultrasound treatment).
Figure 2:
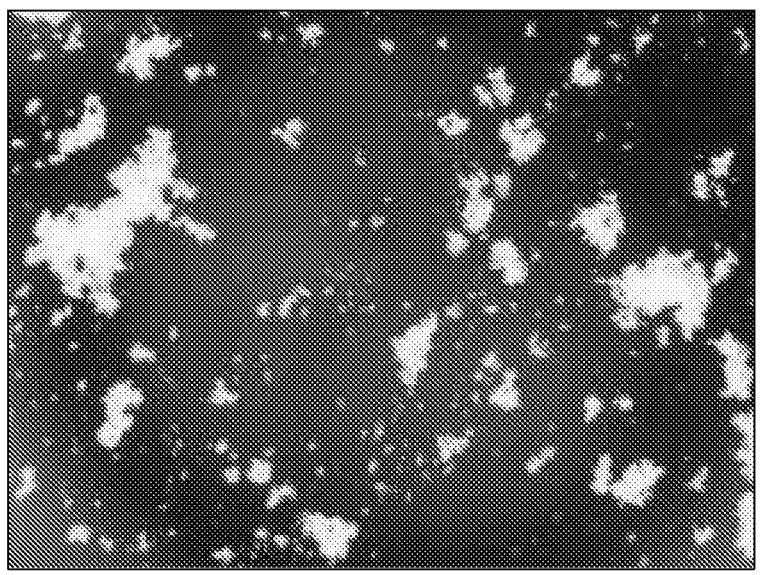
FIG. 2 shows spray dried budesonide with ultrasound treatment according to the present invention.
Figure 3:
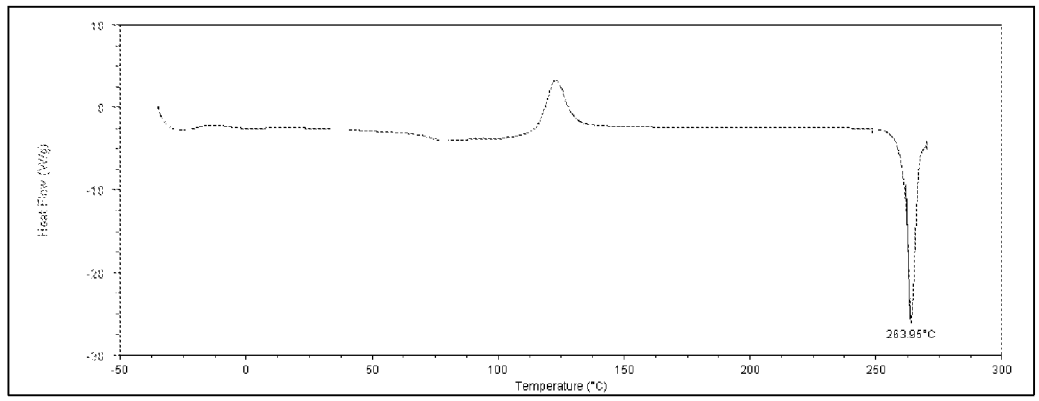
FIG. 3 shows a DSC of conventionally spray dried budesonide.
Figure 4:
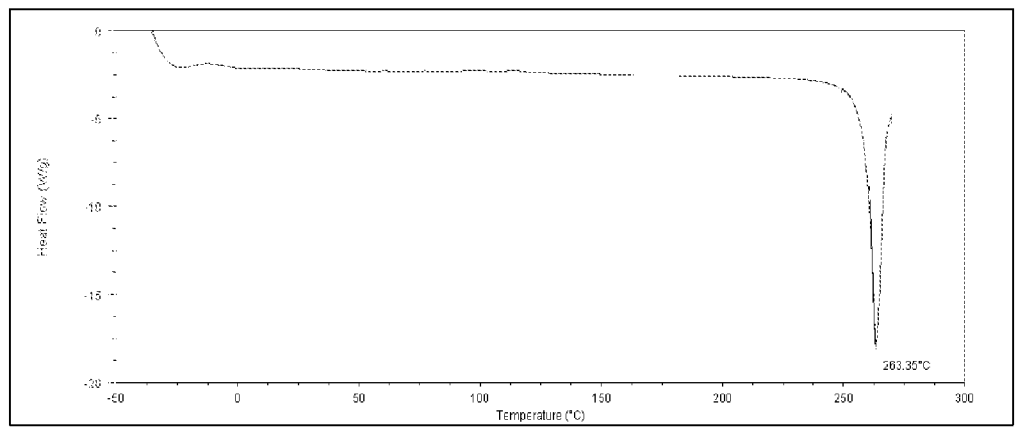
FIG. 4 shows a DSC of spray dried budesonide with dry powder ultrasound treatment of the present invention.

Referring to FIGS. 3 and 4, comparing the DSC traces for the two batches, there is clear indication that application of ultrasound to spray dried particles modifies the physical characteristics of particles. The exotherm (positive peak) at 120° C. is indicative of amorphous to crystalline transformation in the DSC apparatus. In general there is definite improvement in crystalline characteristic of processed material.

Figure 5:
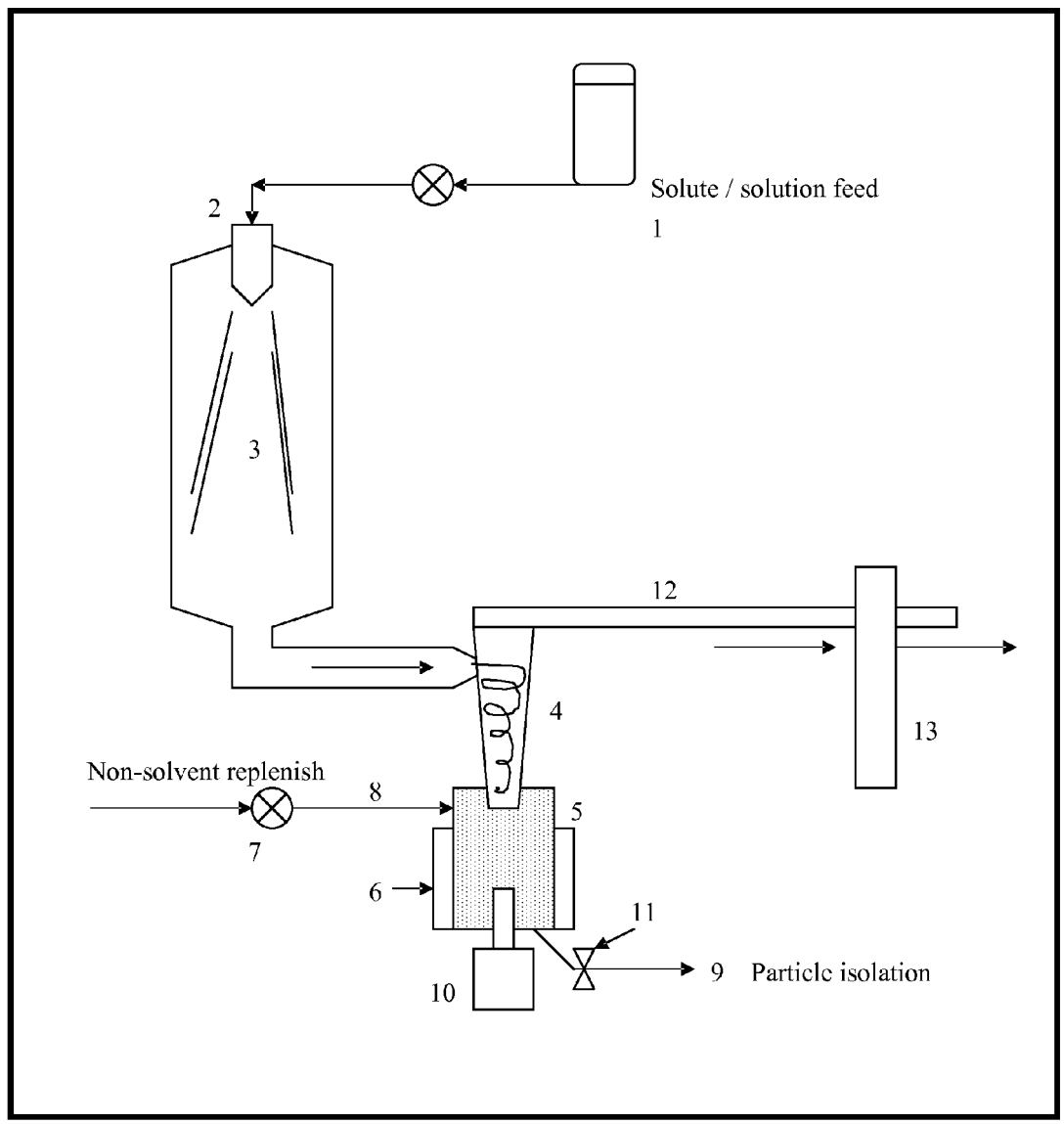
FIG. 5 shows a diagrammatic representation of a conventional spray drying equipment whereby the dry solid collection chamber is replaced by an ultrasonic cell having an ultrasonic probe inserted into the cell.

Turning to FIG. 5, spray drying with ultrasound apparatus comprises a liquid feed chamber 1, spray drying atomiser and heated gas inlet 2, evaporation chamber 3, cyclonic separator 4, continuous ultrasonic treatment chamber 5, (surrounded by a thermal jacket 6). The conventionally treated spray dried powder is deposited directly into an ultrasonic flow cell chamber 5. Concurrently, a continuous feed of non-solvent 7, is pumped via a pump 8, at a suitable flow rate balanced by the rate of flow of particle slurry 9, to subsequent processing by filtration or drying. Ultrasonic probe 10, irradiates the mixture with ultrasonic energy and the mixture flows through an outlet 11. The solvent vapour, ultrafine particles and gases 12, are expelled via filter 13. The ultrasonic radiation is continued as long as necessary until the desired particle size and crystallinity is achieved. Naturally the feed stream to the spray dryer is balanced with the rate at which particle slurry is removed. The flow rates are controlled such that the residence time in the ultrasonic flow cell chamber 5, is for example, 10 s to 1 hr. Localised cavitation occurring on a microscopic scale promotes changes in fluid temperature and pressure that induces the aforementioned solid state effects. By adjusting the power of the ultrasound, and the residence time in chamber 5, the particle size and morphology can be controlled. The ultrasound has the additional benefit that any crystal deposits within the chamber 5, tend to be removed from the surfaces.

Figure 6:
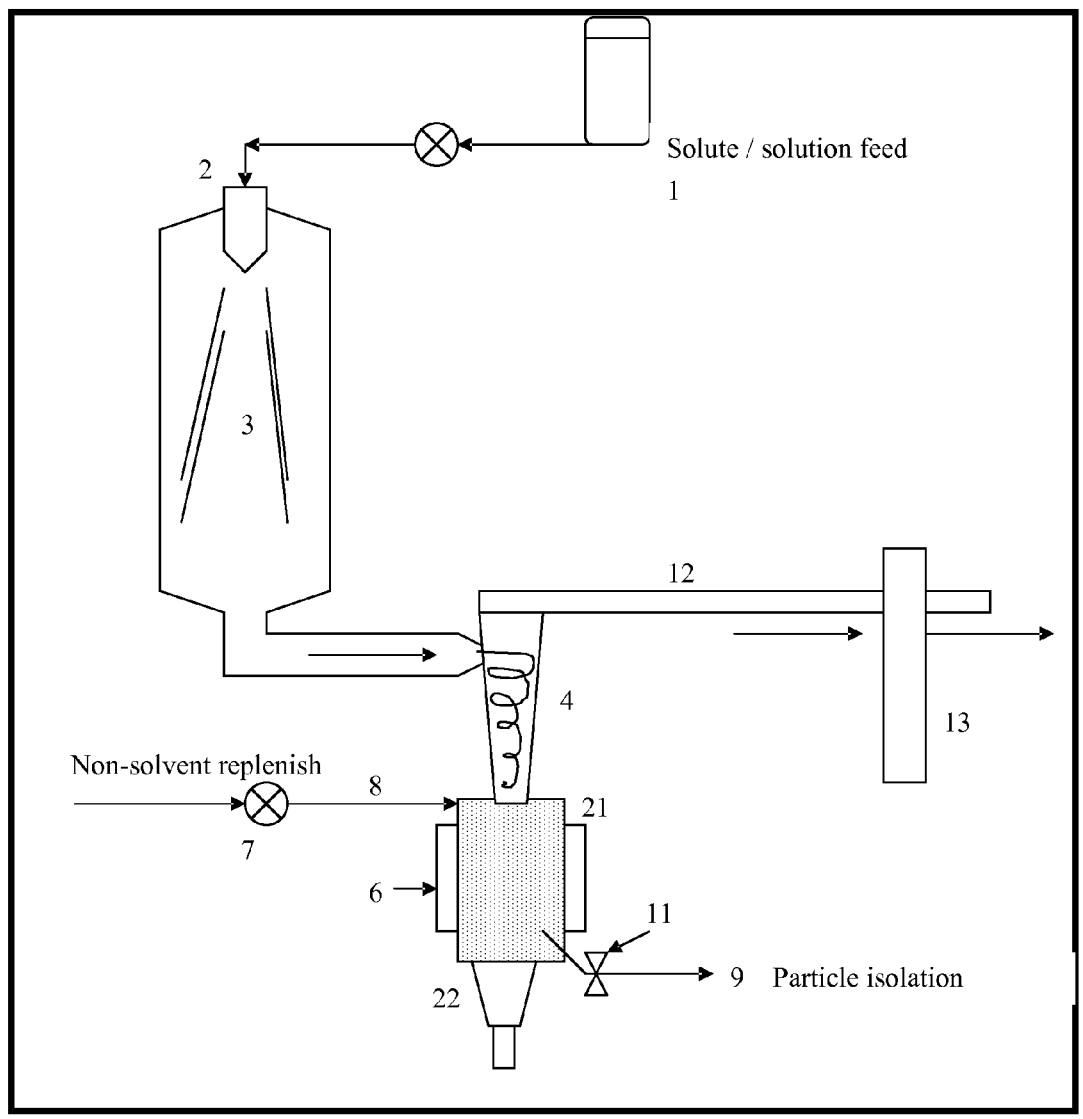
FIG. 6 shows a bonded transducer apparatus of a similar configuration to that of FIG. 5.

Referring to FIG. 6, spray drying with ultrasound apparatus is of a similar configuration to that of FIG. 5 except that chamber 21 has single bonded ultrasonic transducer 22 located on the external surface of it. The transducer 22 insonates the entire volume of the chamber 21 with sufficient intensity to cause dispersion, deagglomeration and amorphous to crystalline or metastable to stable-crystalline conversion, and by adjusting the power of the ultrasound, and the residence time in the chamber 21, the particle size and morphology can therefore be controlled. The ultrasound has the additional benefit that any crystal deposits within the chamber 21 tend to be removed from the surfaces.

Figure 7:
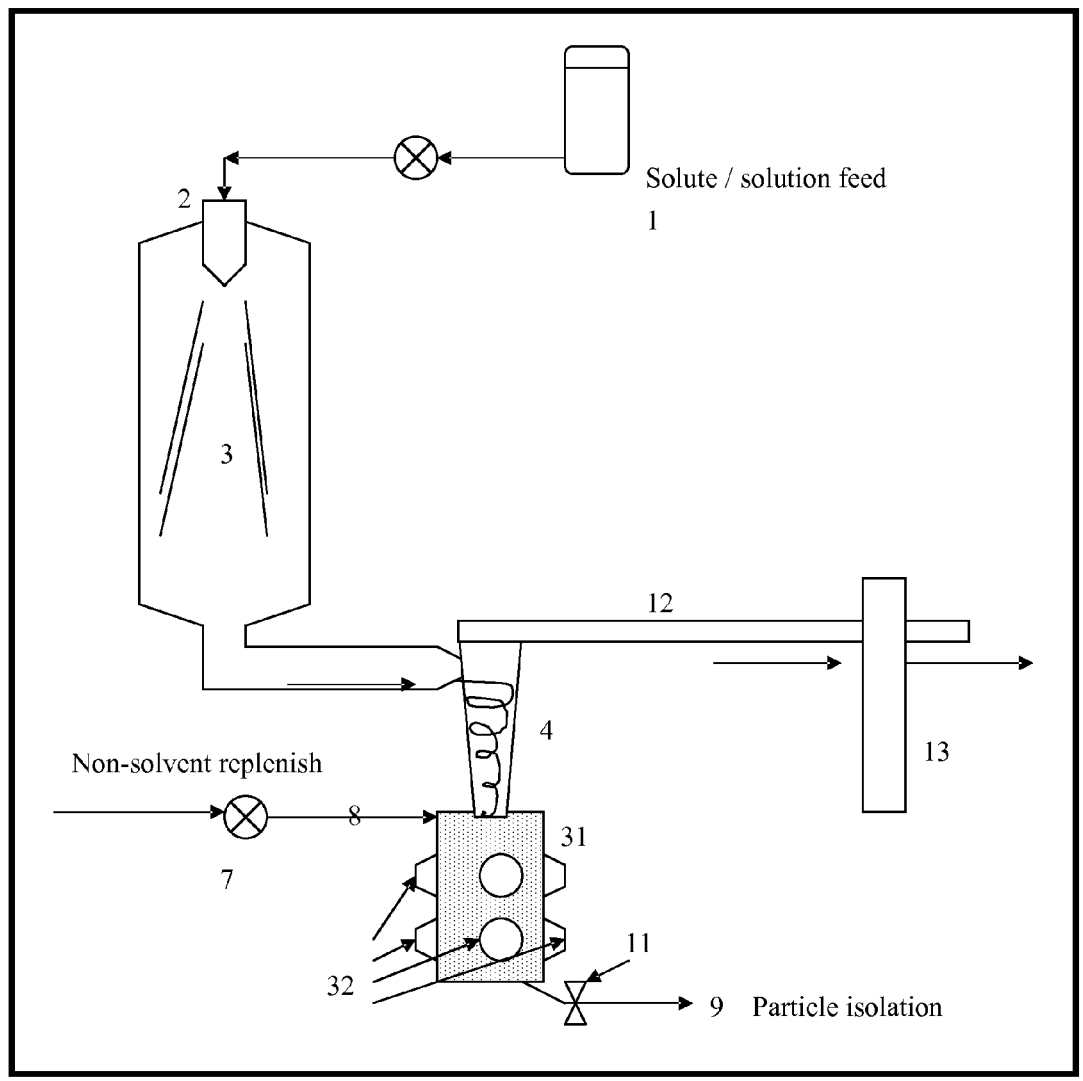
FIG. 7 shows a multiple transducer apparatus of a similar configuration to that of FIGS. 5 and 6. The multiple transducers in this case are circumferentially mounted around a cylindrical duct.

Referring to FIG. 7, spray drying with ultrasound apparatus is of a similar configuration to that of FIGS. 5 and 6 except that chamber 31 has a wrap-around ultrasonic transducers 32 located on the external surface of it. The wrap-around transducers 32 insonates the entire volume of the chamber 31 with sufficient intensity to cause dispersion, deagglomeration and amorphous to crystalline or metastable to stable-crystalline conversion, and by adjusting the power of the ultrasound, and the residence time in the chamber 31, the particle size and morphology can therefore be controlled. The ultrasound has the additional benefit that any crystal deposits within the chamber 31 tend to be removed from the surfaces.

Figure 8:
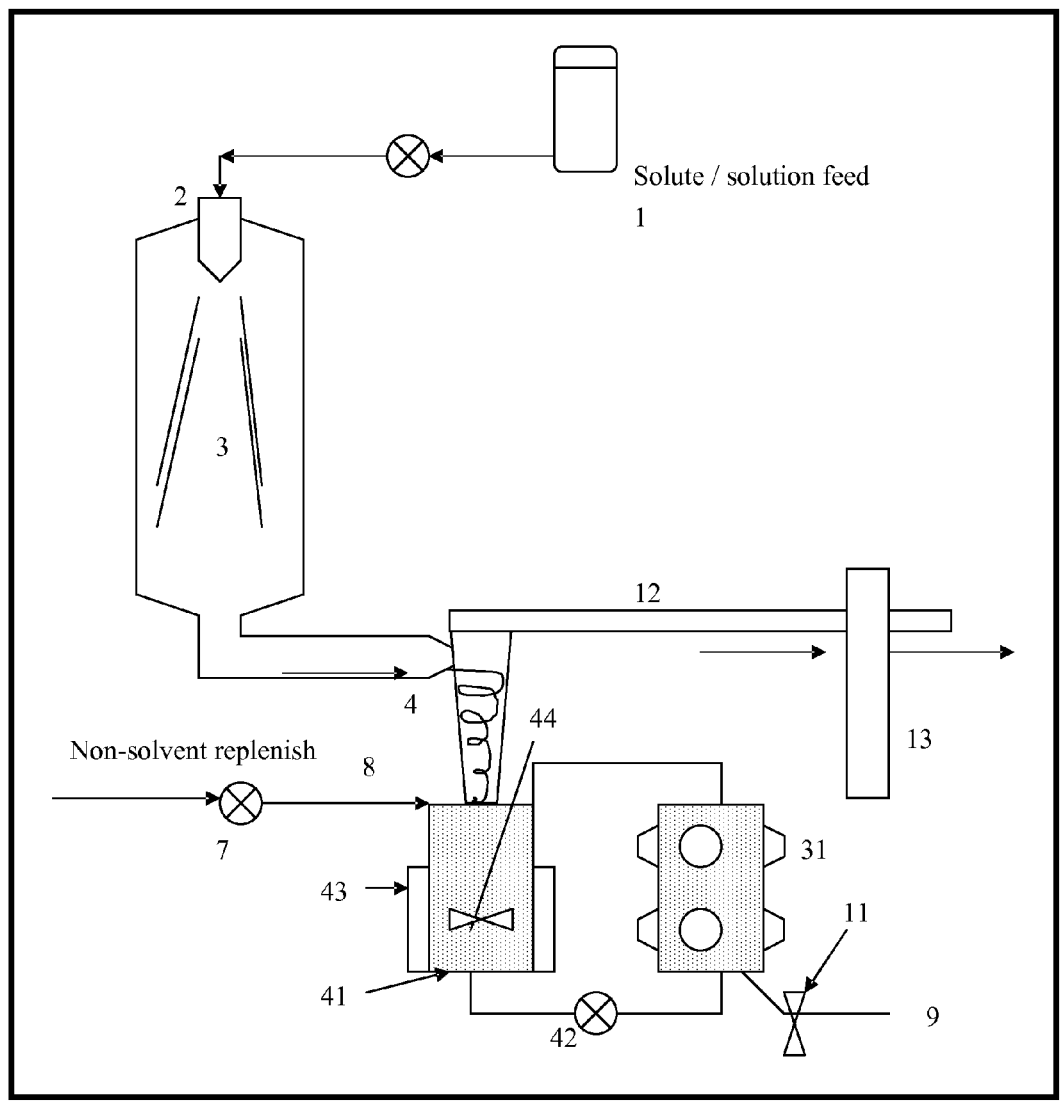
FIG. 8 shows a multiple transducer apparatus similar to that in FIG. 7 where the multiple transducer apparatus is configured in a recirculation loop.

Referring to FIG. 8, this shows a spray drying apparatus with ultrasound apparatus of a similar configuration to that of FIG. 7 except that chamber 31 is attached to a primary particle collection vessel 41 fitted with thermoregulation jacket 43 and optional stirrer impellor 44, via pump 42, thus creating a continuous closed loop processing system. The ultrasound is applied with sufficient intensity to cause dispersion, deagglomeration and amorphous to crystalline or metastable to stable-crystalline conversion, and by adjusting the power of the ultrasound, and the residence time in the recirculation processing loop 31, 41, 42, the particle size and morphology can therefore be controlled.

The skilled addressee will appreciate that the thermal jacket is designed to help maintain the temperature of the non-solvent at a desired temperature, depending on design.

The term "comprising" means "including" as well as "consisting" e.g. a composition "comprising" X may consist exclusively of X or may include something additional e.g. X+Y.

Unless defined otherwise, the word "substantially" does not exclude "completely" e.g. a composition which is "substantially free" from Y may be completely free from Y. Where necessary, the word "substantially" may be omitted from the definition of the invention.

"Optional" or "optionally" means that the subsequently described event of circumstances may or may not occur, and that the description includes instances where said event or circumstance occurs and instances in which it does not.

EXAMPLES

Example 1

Budesonide (5 g) was dissolved in 100 mL of dichloromethane. The samples of budesonide powder collected in the ultrasonic chamber were produced using a Büchi-290 laboratory-scale spray dryer (insulins), Büchi, Switzerland). The solution was atomized using nitrogen at 7 bar flowing at approximately at 10 Lpm (Liter/minute). The aspirator was set at 100% and flow rate of solution was set to 10 Lpm. The gas temperature was set to 120° C. Budesonide particles were collected the ultrasonic chamber connected to the end of high performance cyclone separator. In order to apply ultrasound to the spray dried particles, the collection ultrasonic chamber was filled with heptane thermoregulated at 25° C. and was fitted with an ultrasonic probe resonating at 20 kHz. Ultrasound at 20 W power was applied between 30 minutes and 1 hour. The resulting particle slurry was spray dried and particles characterized by optical microscopy and DSC (Differential Scanning calorimetry). The size of the particles were typically in the range of 1-7 μm.

The D(10), D(50), D(90) for two representative samples were 1.21, 3.03, 4.63 μm and 1.05, 2.99, 3.76 μm respectively as determined by Sympatec HELOS laser diffraction.

Differential Scanning Calorimetry

DSC experiments were performed with a DSC Q2000 V24.2 build 107 (TA Instruments, UK). Approximately 3 mg of material was weighed into the sample pan of the DSC and subjected to heating ramp of 100° C./min add heated to 275° C. The DSC measurement was carried out using the following steps.

Run 9 (spray dried material not treated with ultrasound according to the present invention)
Instrument DSC Q2000 V24.2 Build 107
Module DSC Standard Cell RC
Sample px02-262-spray dried
Size 2.140 mg
Method Fast Heating expt 100° C.-min
Weighed sample is heated at rate of 100° C./Min to 275° C.

Run 10 (material treated with ultrasound according to the process of the present invention)
Instrument DSC Q2000 V24.2 Build 107
Module DSC Standard Cell RC
Sample px02-262-post ultrasound
Size 3.590 mg
Method Fast Heating expt 100° C.-Min
Weighed sample is heated at rate of 100° C./Min to 275° C.

Example 2

Example 2 shows the advantages of the particles produced according to the present invention.

Figure 9:
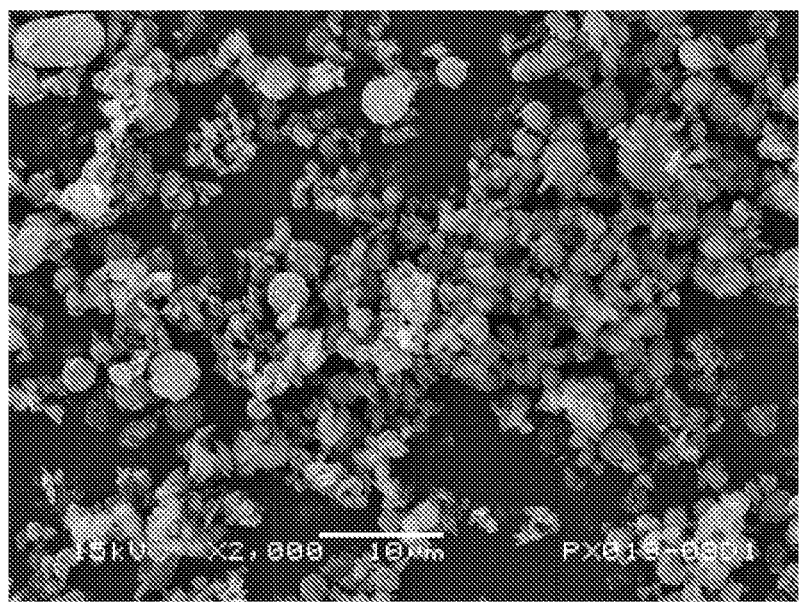
FIG. 9 shows a sample of fluticasone propionate prepared by aerosolisation (according to the invention).

The aerosolisation efficiency of three batches of engineered fluticasone propionate (FP) produced by various processing was assessed in binary dry powder inhaler (DPI) formulations. Batches studied include:

Sample 2 Prepared by aerosolistion method exemplified in this invention as shown in SEM FIG. 9. Fluticasone propionate (4 g) was dissolved in 100 mL of acetone. The samples of Fluticasone propionate powder collected in the ultrasonic chamber were produced using a Büchi-290 laboratory-scale spray dryer (Büchi, Switzerland). The solution was atomized using nitrogen at 7 bar flowing at approximately at 10 Lpm (Liter/minute). The aspirator was set at 100% and flow rate of solution was set to 10 Lpm. The gas temperature was set to 120° C. Fluticasone propionate particles were collected the ultrasonic chamber connected to the end of high performance cyclone separator. In order to apply ultrasound to the spray dried particles, the collection ultrasonic chamber was filled with heptane thermoregulated at 25° C. and was fitted with multiple bonded transducers (akin to FIG. 7) resonating at 20 kHz. Ultrasound at 20 W power was applied between 30 minutes and 1 hour. The resulting particle slurry was spray dried and particles characterized by optical microscopy and DSC (Differential Scanning calorimetry). The size of the particles were typically in the range of 1-6 μm. The D(10), D(50), D(90) were 1.35, 3.25, 5.63 μm as determined by Sympatec HELOS laser diffraction.

Figure 10:
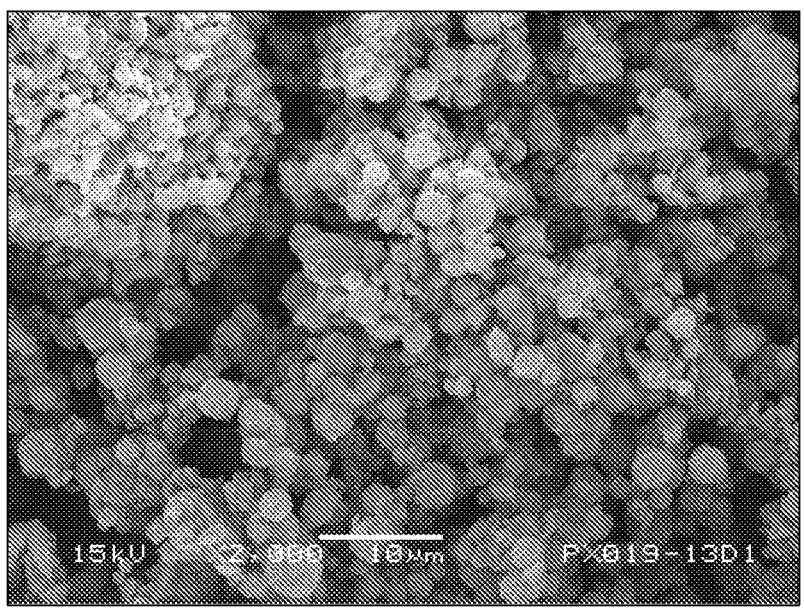
FIG. 10 shows a sample of fluticasone propionate prepared by aerosolisation (according to the invention).

Sample 3 Prepared by aerosolistion method exemplified in this invention as shown in SEM FIG. 10. Sample 3 was prepared by the same method as sample 2, except that 3 g of FP was used in sample 3. The D(10), D(50), D(90) were 0.99, 2.55, 4.97 μm as determined by Sympatec HELOS laser diffraction.

Figure 11:
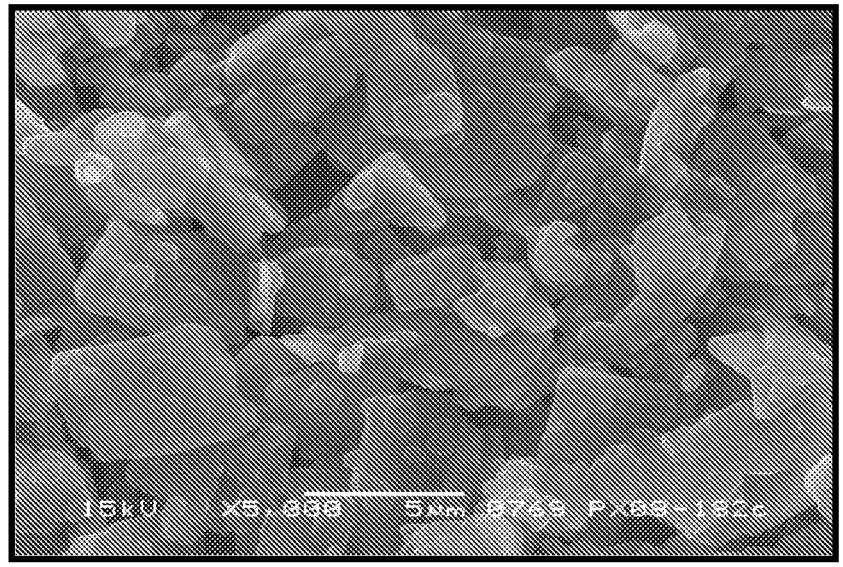
FIG. 11 shows a sample of fluticasone propionate prepared by dispersion and precipitation with ultrasound.
Figure 12:
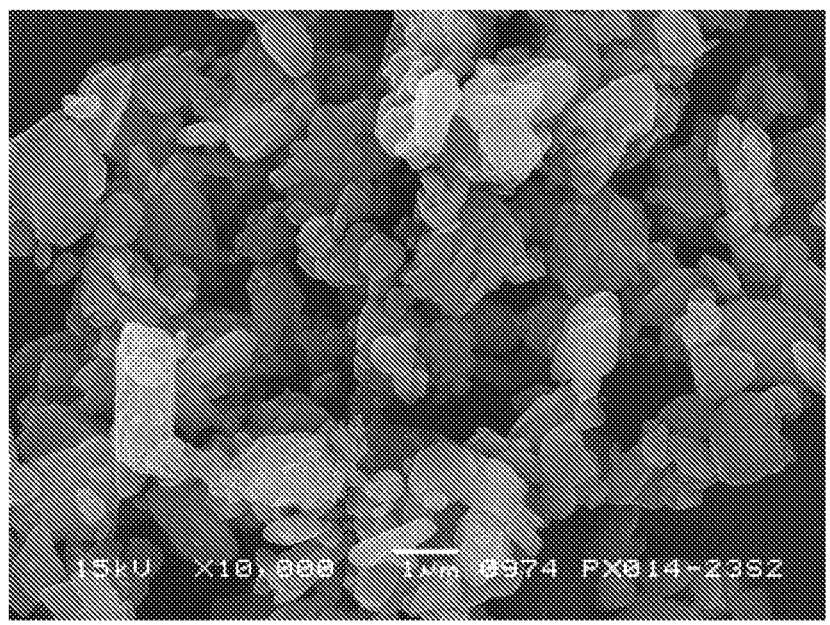
FIG. 12 shows a sample of micronised/milled fluticasone propionate.

Sample 4 Prepared by alternative precipitation approach as shown in SEM FIG. 11. Sample 4 was prepared as described in WO 2008/114052 A1. This method does not use initial solution atomization. Instead this prior art involves the dispersive antisolvent crystallization brought about by adding a solution of fluticasone propionate in acetone to heptane antisolvent in the presence of an ultrasonic field. This leads to particles significantly smoother than particles formed using the method of the current invention. The D(10), D(50), D(90) were 1.14, 2.67, 5.11 μm as determined by Sympatec HELOS laser diffraction.

The samples were compared to an additional binary DPI formulation containing micronized FP and formulations extracted from a Flixotide Discus inhaler.

The aerosolization efficiency of samples 2, 3 and 4 of engineered FP were evaluated using binary formulations containing 0.4% w/w FP.

Each binary formulation contained 0.016 g FP and 3.984 g lactose (ML001, DMV-Fonterra, Vehgel, Netherlands) and was prepared by geometric mixing. Following this, the blend was subsequently prepared using a Turbula T2F (Willy A Bachofen A G, Basel, Switzerland) at 46 rpm for 45 minutes.

Following content uniformity testing, 12.5±1 mg of each blend was loaded into size 3 hydroxypropylmethyl cellulose capsules (HPMC, Shionogi Qualicaps S A, Basingstoke, UK). The capsules were stored at 44% RH for 24 h prior to in vitro performance testing.

Testing was performed using a Next Generation Impactor (NGI) with pre-separator, which was connected to a vacuum pump (GE Motors). Prior to testing, the pre-separator was filled with 15 ml of mobile phase and the cups of the NGI cups were coated with 1% v/v silicone oil in hexane to eliminate particle bounce.

For each experiment, four individual capsules of the same formulation were discharged into the NGI at 60 Lpm for 4 s via a Rotahaler (GSK, Ware, UK) DPI device. Additionally, blisters from a Flixotide Diskus (GSK, Ware, UK) were emptied and loaded into size 3 HPMS capsules and discharged into a NGI at 60 Lpm1 for 4 s via a Rotahaler. Following aerosolization, the NGI apparatus was dismantled and the inhaler, capsules and each part of the NGI was washed down into known volumes of HPLC mobile phase.

The mass of drug deposited on each part of the NGI was determined by HPLC. This protocol was repeated three times for each blend, following which, the mass median aerodynamic diameter (MMAD), geometric standard deviation (GSD), fine particle dose (FPD) and fine particle fraction of the emitted dose (FPFED) were determined. The FPD represented the mass of drug that was collected on stages 3-8 of the NGI.

The aerosolization efficiency is shown in FIG. 13. The percentage fine particle fraction is shown in FIG. 14.

The aerosolisation efficiency as determined by percentage fine particle fraction (% FPF) of Samples 2 and 3 was significantly greater than that of micronized FP. This data is shown in FIG. 15 and clearly displays aerosol efficiency compared with the formation from a Flixotide. The increase in the performance on inclusion of these materials was dramatic for the inhaler used in this study. Sample 4 had a significantly lower % FPF than micronized FP, which was related to the surface morphology of the particles. These data suggested little difference between the aerosolisation efficiency of samples 2 and 3.

Comparative in vitro data shows that the performance of particle produced according to the present invention are overwhelmingly and surprisingly superior to performance of both conventionally milled particles and specially prepared (ultrasonically precipitated) particles that have vastly different surface, and geometric properties. In all cases the particles have the same particle size range. In a specific example for Fluticasone propionate, the FPF for optimal particles was 54% greater than micronized/milled and over 200% greater than precipitated material. The significant differences and improved performance of these optimal particles can therefore be attributed not to size, although this is an important design criterion, but a range of other properties that describe these vastly improved particles.

The SEM images shown in FIGS. 9 and 10 (according to the invention) clearly show clear contrast in terms of shape and surface roughness compared to precipitated and milled material shown in FIGS. 11 and 12 respectively (not according to the invention). The roughness and rounded/spheroid 3D shape has a profound impact on their performance.

All formulations were stored for one and three months at 25° C./75% RH. The FPF of the formulation containing micronized fluticasone propionate decreased by almost 50% after storage for one month and almost 70% after storage for three months compared to the FPF at t=0. However, the FPF of formulations containing particles prepared by the current invention were not as affected following storage in stress conditions. The FPF of sample 3 decreased 6% after storage for one month and decreased 3% after storage for three months compared to the FPF at t=0. The FPF of sample 2 decreased 7% after one months storage and 28% after three months storage compared to the FPF at t=0. There was a small yet statistically significant decrease, 29%, in the fine particle fraction of the formulation containing sample 4 which was prepared by alternative precipitation approach after one month with a decrease of 24% after 3 months storage compared to the FPF at t=0. This may be related to the planar morphology of the particles, and therefore, the particles are likely to develop greater adhesion to the lactose as result of capillary forces. The data are shown in FIGS. 23 and 24. It is clear that the FPF of samples 2 and 3 maintained a higher FPF than the micronized sample or sample 4 when stored for one or three months in the conditions described. The FPF of samples 2 and 3 decreased by a smaller percentage than the micronized sample when stored for one or three months in the conditions described. This shows that samples 2 and 3 were more stable than the micronized sample after storage for one or three months. Sample 4 has a much lower FPF than samples 2 and 3 after storage for one or three months.

Example 3

Example 3 shows the advantages of the particles produced according to the present invention for formulation in a pMDI. FIG. 25 is a particle fraction distribution graph for various stages on the NGI and clearly shows the superior performance in terms of FPF for sample 1 and sample 5. Both samples were produced in a similar manner to sample 2 of Example 2. Sample 1 was prepared from atomization of a 3% solution of fluticasone propionate in 20% dichloromethane in methanol (3 g in 100 ml) and Sample 5 was prepared from atomization of 3% solution in acetone (3 g in 100 ml). As shown in FIG. 25, the FPF on stage 5 (cut-off 1.36 μm) of the NGI for both samples showed over 100% increase compared with micronized material, alongside similar FPF for stage 4 (cut-off 2.30 μm). The FPF values were 11.80% and 13.80% on stage 5 for samples 5 and 1 respectively compared with 6.20% for micronized material. It is clear therefore, that samples 1 and 5 have a similar FPF to the micronized product at stage 4, and a greater FPF than the micronized product at stage 5.

Example 4

The aerosolisation efficiency of samples 2, 3 and 4 of fluticasone propionate (FP) produced as described in Example 2 was assessed in combination dry powder inhaler (DPI) formulations containing micronized salmeterol xinafoate (SX) using a Rotahaler® unit dose DPI device (GSK, Ware, UK) and Cyclohaler® unit dose DPI device (TEVA Pharmaceuticals, Netherlands).

The aerosolization efficiency was evaluated in combination DPI formulations also containing micronized SX. Each combination formulation contained 0.16000 g FP (sample 2, 3 or 4), 0.02320 g SX and 3.8168 g lactose (ML001, DMV-Fonterra, Vehgel, Netherlands) and was prepared by geometric mixing. Following this, each blend was subsequently prepared using a Turbula T2F (Willy A Bachofen A G, Basel, Switzerland) at 46 rpm for 45 minutes. The blend strength of each combination formulation equated to 500 μg FP and 50 μg Salmeterol base. This matches the dose strength of Advair 500/50. A sample of Advair 500/50 was used as the micronized example. The aerolisation efficiency of four different formulations containing FP samples 2, 3, 4 or micronized FP was measured.

Figures 25, 26:
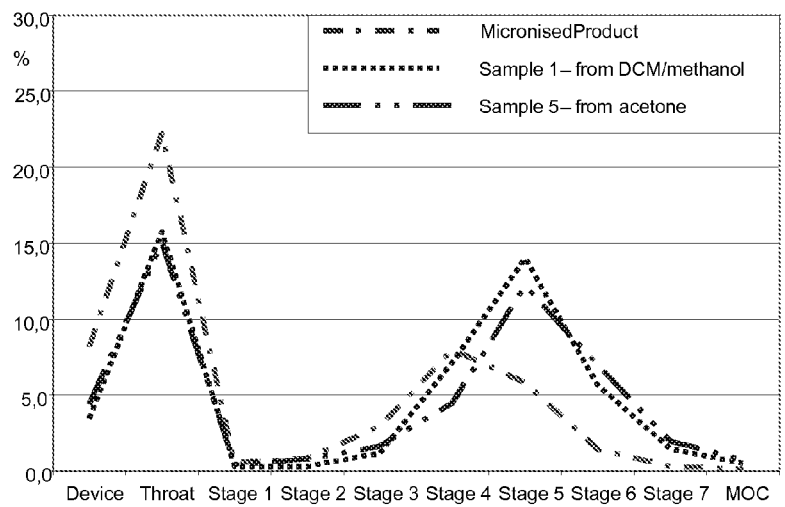
FIG. 25 shows a particle fraction distribution graph for various stages of a Next Generation Impactor.
FIG. 26 shows the fine particle fraction of various samples of fluticasone propionate following 1 month storage.

As shown in FIG. 26, at T=0, the FPF of samples 2, 3 and 4 using a Cyclohaler unit dose DPI device are greater than the micronized sample. When the Rolahaler unit dose DPI device is used, the FPF of samples 2 and 3 is greater than sample 4 and the micronized sample. This shows that the fluticasone propionate particles of the present invention, samples 2 and 3, overall have a higher FPF in the two devices. While sample 4 performs well in the Cyclohaler unit, it has a poor performance in the Rolahaler unit. Samples 2 and 3 have a high FPF in both units.

The four samples were stored for 1 month at 25° C./75% RH. The % FPF of micronized FP and the samples 2, 3 and 4 was not significantly affected under stressed storage conditions. These data show that particles prepared by the current invention should afford stability to DPI formulations.

Following content uniformity testing, 12.5±0.5 mg of each blend was loaded into size 3 hydroxypropylmethyl cellulose capsules (HPMC, Shionogi Qualicaps S A, Basingstoke, UK). The capsules were stored at 44% RH for 24 h prior to in vitro performance testing.

Testing was performed using a Next Generation Impactor (NGI) with pre-separator, which was connected to a vacuum pump (GE Motors). Prior to testing, the pre-separator was filled with 15 ml of mobile phase and the cups of the NGI cups were coated with 1% v/v silicone oil in hexane to eliminate particle bounce.

For each experiment, two individual capsules of the same formulation were discharged into the NGI at 60 Lpm for 4 s via a Rotahaler (GSK, Ware, UK) and 90 Lpm for 2.8 s via a Cyclohaler (TEVA Pharmaceuticals, Netherlands) to ensure both devices were operated such that 4 kPa pressure drop was generated.

Additionally, blisters from a commercially available Advair 500/50 Diskus (GSK, USA) were emptied and 12.5 mg of formulation was transferred into size 3 HPMC capsules and discharged into a NGI at 60 Lpm for 4 s via a Rotahaler and at 90 Lpm for 2.8 s via a Cyclohaler.

Following aerosolization, the NGI apparatus was dismantled and the inhaler, capsules and each part of the NGI was washed down into known volumes of HPLC mobile phase. The mass of drug deposited on each part of the NGI was determined by HPLC. This protocol was repeated three times for each blend, following which, the fine particle dose (FPD) and fine particle fraction of the loaded dose (FPFLD) were determined. The FPD represented the mass of drug that was collected on stages 3-8 of the NGI.

Figure 27:
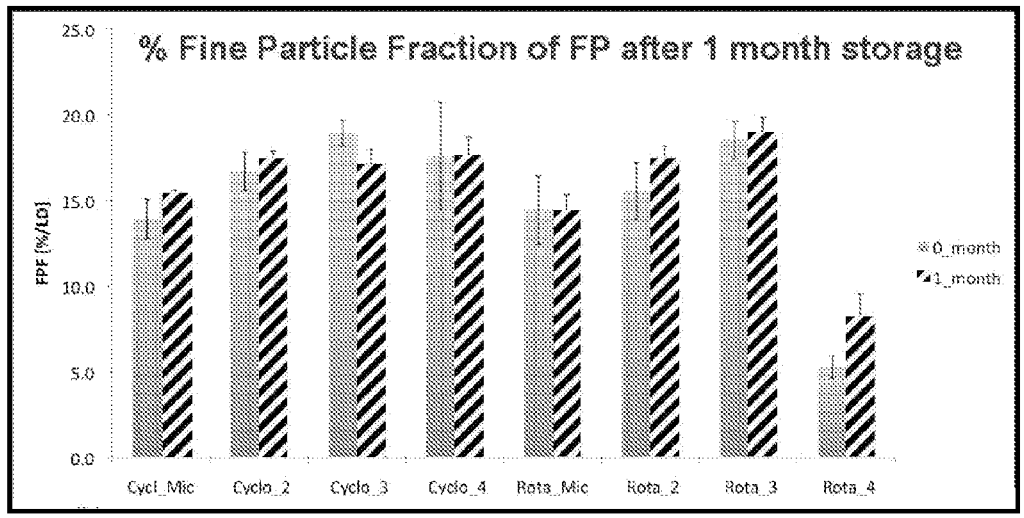
FIG. 27 shows a bar chart representation of fine particle fraction.

FIG. 26 shows the FPF specifically for FP for an Advair 500/50 equivalent blend of FP, prepared according to this example, and mechanically micronized SX particles. FIG. 27 graphically shows the FPF performance of particles whereby the FP was prepared by this invention. Samples 2 and 3 (cyclo_2 and cyclo_3, and rota_2 and rota_3) clearly show superior performance in terms of FP, and thus clearly indicates that the cohesion between FP and FP particles and adhesion of lactose to FP can be controlled. Above all the micronized components used in this study are from commercially available devices whereby the micronized material has undergone several weeks if not months of conditioning. Conversely particles made by the current invention are highly stable even when freshly prepared, and to reiterate, this again states that particles prepared by the current invention should afford stability to DPI formulations.

Figure 28:
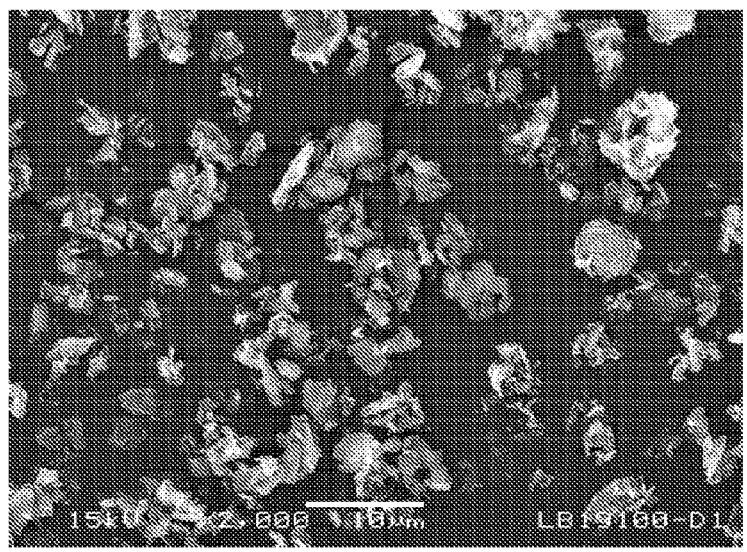
FIG. 28 shows fluticasone propionate particles (90% by weight) made by the current invention in combination with salmeterol xinafoate particles (10% by weight).

FIG. 28 shows particles of FP sample 3 made by the current invention. They were then blended into a combination consisting of salmeterol xinafoate (10% by weight) and fluticasone propionate (90% by weight), wherein the salmeterol xinafoate particles were micronized and the fluticasone propionate particles are prepared according to the present invention.

Example 5

The cohesive-adhesive balance (CAB) of micronized Fluticasone Propionate (FP) and batches of FP engineered by the method of the current invention (samples 2 and 3) and by a different method exemplified in WO 2008/114052 A1 (sample 4), as described in Example 1, were determined with respect to crystalline substrates of FP and lactose monohydrate. The CAB force balance of the different batches with respect to the crystalline substrates was determined as follows:

Probe Preparation:

Particles (n=3) of all batches of FP were attached onto standard V-shaped tipless cantilevers (DNP-020, DI, CA, USA) using an epoxy resin glue (Araldite, Cambridge, UK).

Production of Smooth Lactose & Drug Crystals:

Smooth crystals of lactose were produced on cooling of a heated saturated droplet sandwiched between cover slips. Smooth drug crystals were produced using sitting-drop anti-solvent crystallisation, in which the active was dissolved in acetone and the anti-solvent employed was water.

AFM Force Measurements:

Individual force curves (n=1024) were conducted over a 10 μm×10 μm area at a scan rate of 4 Hz and a compressive load of 40 nN. Environmental conditions were maintained at a constant temperature of 20° C. (±1.5° C.) and relative humidity 45±3%.

The CAB analysis of micronized FP suggested that for equivalent contact geometry, the adhesive FP-Lactose interactions of micronized FP are 1.36 times greater than the cohesive FP-FP interactions.

The CAB analysis of sample 2 FP suggested that for equivalent contact geometry, the adhesive FP-Lactose interactions of sample FP are 1.17 times greater than the cohesive FP-FP interactions.

The CAB analysis of sample 3 FP suggested that for equivalent contact geometry, the adhesive FP-Lactose interactions of sample 3 FP are 1.16 times greater than the cohesive FP-FP interactions.

The CAB analysis of sample 4 FP suggested that for equivalent contact geometry, the adhesive FP-Lactose interactions of sample 4 FP are almost equal to the cohesive FP-FP interactions.

Figures 29, 30:
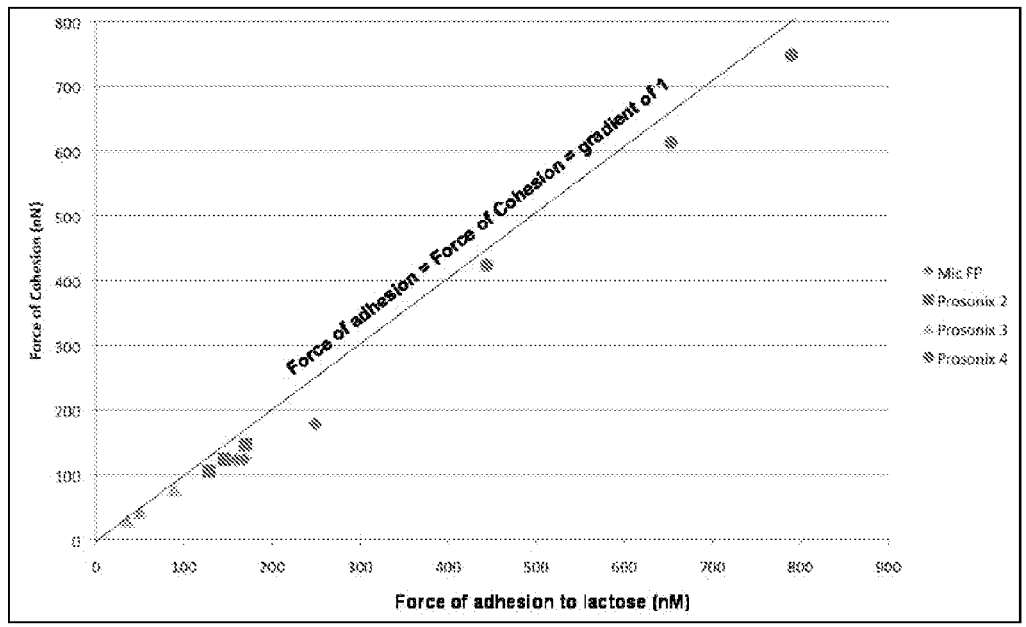
FIG. 29 shows the cohesive-adhesive balance of fluticasone propionate with lactose.
FIG. 30 shows the excellent homogeneity of FP particles of the present invention when blended with micronized SX.

As shown in FIG. 29, the micronized FP was significantly more adhesive to lactose than samples 2, 3 and 4 of FP prepared. Sample 4 was the least adhesive to lactose and SX and therefore, suggests that the surface energy of this material is significantly different from the other batches. However, the adhesion values ranged between 400-800 nN, which reflects the greater contact radius of particles of this material when contacting the different substrates. The greater contact radius of this material will result in limited aerosolisation upon formulation of sample 4 in dry powder inhaler (DPI) formulations.

In contrast, the adhesion values relating to FP—lactose interaction of sample 3 ranged from 35-89 nN and the adhesion values of sample 2 ranged from 128-169 nN, which reflects the smaller contact radius of particles of the present invention when contacting the different substrates. The small contact radius of this material will result in greater FP aerosolisation upon formulation of samples 2 and 3 in carrier-based DPI formulations compared to micronized FP, with adhesion values ranging from 169-249 nM.

CAB analysis confirmed that sample 3 may have smaller contact radii than the other materials, whereas sample 4 may have greater contact radii, which is related to the surface geometry of these particles.

These data demonstrate that the particle engineering strategy as exemplified by this invention are able to afford control on both surface energy and particle contact geometry, both of which are critical quality attributes of drug particles in DPI formulations.

FIG. 29 shows the FP-Lactose interactions with respect to different contact geometry of particles taking note of the relatively high forces of both adhesion and cohesion for sample 4.

Example 6

The aerosolization efficiency of sample 3 of fluticasone propionate (FP) produced as described in Example 2 was assessed in combination dry powder inhaler (DPI) formulations containing micronized salmeterol xinafoate (SX) using a Rotahaler® unit dose DPI device (GSK, Ware, UK) and Cyclohaler® unit dose DPI device (TEVA Pharmaceuticals, Netherlands).

The aerosolization efficiency was evaluated in combination DPI formulations also containing micronized SX. Each combination formulation contained 0.16000 g FP, 0.01160 g SX and 3.8284 g lactose (ML001, DMV-Fonterra, Vehgel, Netherlands) and was prepared by geometric mixing. Following this, the blend was subsequently prepared using a Turbula T2F (Willy A Bachofen A G, Basel, Switzerland) at 46 rpm for 45 minutes. The blend strength of the combination formulation equated to 500 µg FP and 25 µg Salmeterol base, therefore this was a 500/25 formulation.

Assessment of the content uniformity of the formulation containing micronized FP and micronized SX with a 500/25 formulation suggested poor homogeneity and therefore, this formulation was not characterised by in vitro impaction studies. In contrast, the formulation containing FP sample 3 and micronized SX exhibited very good homogeneity as shown in FIG. 20. This shows the % Relative Standard Deviation for Sample 3 for FP was 3.43 and for SX was 4.55. This compared to the micronized FP-SX formulation, where the % Relative Standard Deviation of FP was 8.76 and of SX was 15.95.

Following content uniformity testing, 12.5±0.5 µg of the blend containing the FP sample 3 blend or Advair was loaded into size 3 hydroxypropylmethyl cellulose capsules (HPMC, Shionogi Qualicaps S A, Basingstoke, UK). The capsules were stored at 44% RH for 24 h prior to in vitro performance testing.

Testing was performed using a Next Generation Impactor (NGI) with pre-separator, which was connected to a vacuum pump (GE Motors). Prior to testing, the pre-separator was filled with 15 ml of mobile phase and the cups of the NGI cups were coated with 1% v/v silicone oil in hexane to eliminate particle bounce.

For each experiment, two individual capsules of the same formulation were discharged into the NGI at 90 Lpm for 2.8 s via a Cyclohaler (TEVA Pharmaceuticals, Netherlands) to ensure both devices were operated such that 4 kPa pressure drop was generated.

Following aerosolization, the NGI apparatus was dismantled and the inhaler, capsules and each part of the NGI was washed down into known volumes of HPLC mobile phase. The mass of drug deposited on each part of the NGI was determined by HPLC. This protocol was repeated three times for each blend, following which, the fine particle dose (FPD) and fine particle fraction of the loaded dose (FPFLD) were determined. The FPD represented the mass of drug that was collected on stages 3-8 of the NGI.

Figure 21:
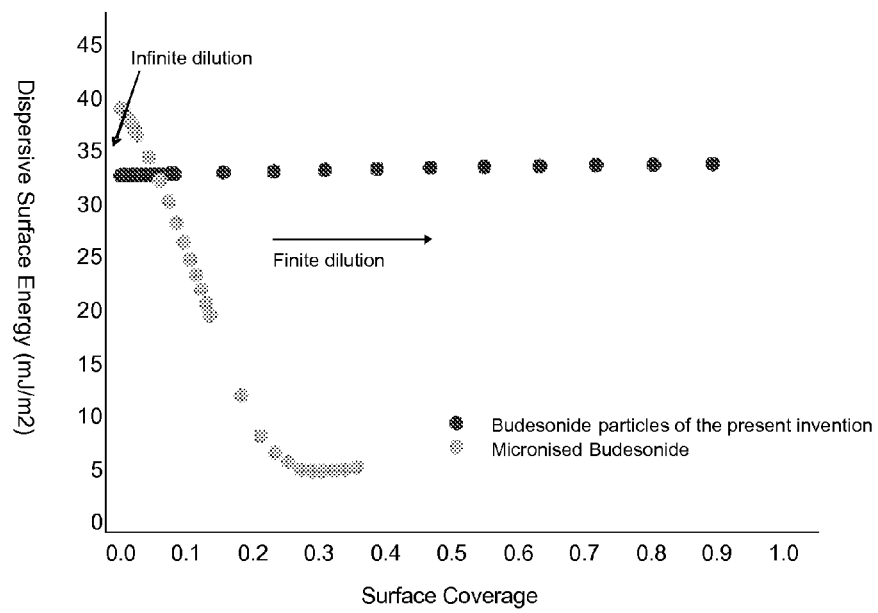
FIG. 21 Surface energy measurements with IGC at finite and infinite dilution.
Figure 22:
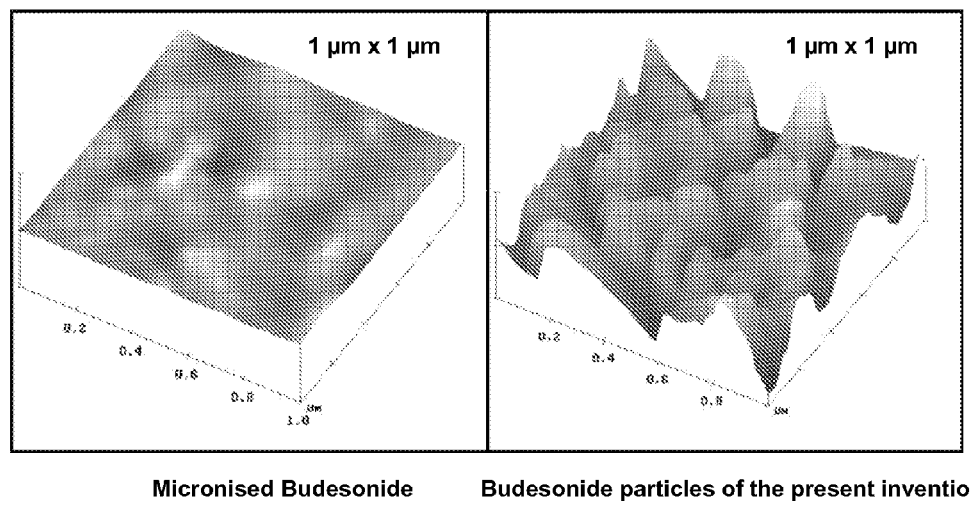
FIG. 22 AFM Topology profiles for budesonide micronized and particles of the present invention.

Performance data suggested a FPD for sample 3 in a 500/25 formulation of 79 µg and 11 µg for FP and SX, respectively as shown in FIG. 30. As shown in FIG. 21 this translated to a fine particle fraction of 44% for SX compared with 15.8% for the engineered FP.

Figure 31:
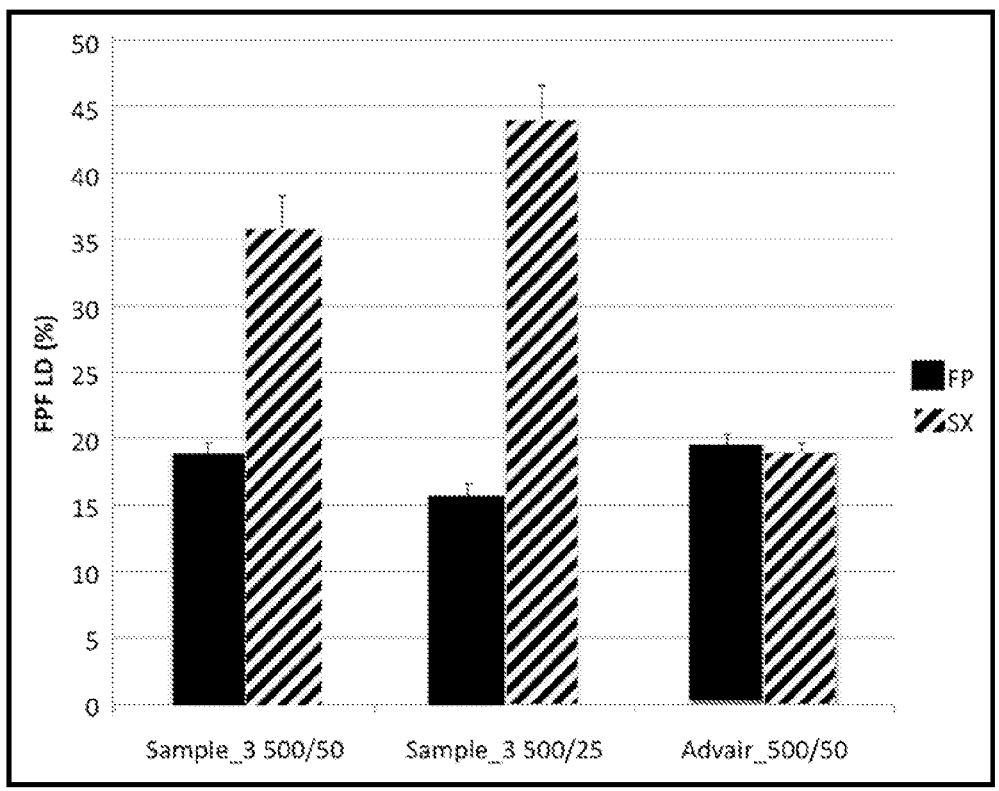
FIG. 31 shows the FPFLD for FP engineered according to the current invention when blended with micronized SX compared with Advair.

FIG. 31 shows the FPFLD measured as described above, for formulations containing 500 µg of Sample 3 FP and 50 µg of SX (Sample_3 500/50), 500 µg of Sample 3 FP and 25 µg of SX (Sample_3 500/25) and Advair (Advair_ 500/50) which contained 500 µg of FP and 50 µg of SX. This Figure shows that in Sample_3 500/50 and Sample_3 500/25, SX had a much higher FPFLD than Advair_500/50. The FPFLD of SX of the Sample_3 500/25 was higher than the Sample_3 500/50.

This implies that the engineered FP has a dramatic effect on both the content uniformity of the blend and facilitates an increase in SX with respect to FPF, also implying that for a given formulation using engineered FP significantly less SX can be used in the blend to achieve comparable FPF for both FP and SX. These data suggest that using engineered FP, prepared by the current invention, it is possible to formulate combination DPI products containing half of the nominal strength currently deployed in the Advair product.

Example 7

The surface roughness and surface area of micronized Fluticasone Propionate (FP), sample 3 of FP prepared by the current invention and sample 4 of FP, as described in Example 2, were determined using atomic force microscopy (AFM) and BET surface area analysis, respectively. The roughness of imaged areas was quantified using the mean ($R_a$) and root mean square ($R_q$) of the variations in the height of the imaged surface. Furthermore, the surface area of samples was determined by a five-point BET nitrogen adsorption analysis.

The surface topography of the FP samples was investigated with TappingMode™ atomic force microscopy (AFM) using a Multimode AFM, J-type scanner, Nanoscope IIIa controller (all from DI, Cambridge, UK) and a silicon tip (model number OMCL-AC240TS, Olympus, Japan) to image three randomly selected 1 µm×1 µm square areas on the surface of particles of each material with a resolution of 512×512 pixels and a scan rate of 1 Hz. The roughness of imaged areas was quantified using the mean ($R_a$) and root mean square ($R_q$) of the variations in the height of the imaged surface, as calculated by the AFM software using the following equations:

$$R_a = \frac{1}{n_p} \sum_{i=1}^{n} |y_i|$$

$$R_q = \sqrt{\frac{1}{n_p} \sum_{i=1}^{n} y_i^2}$$

where $n_p$ is the number of points in the image and $y_i$ is the distance of point i from the centre line.

The specific surface areas of the FP samples were measured using a Gemini 2360 surface area analyser (Micromeritics Instrument Corporation, Norcross, USA). A five-point BET nitrogen adsorption analysis was carried out after degassing the samples for 24 hours in a FlowPrep 060 degasser (Micromeritics Instrument Corporation, Norcross, USA).

The results are summarised in Table 2 below:

TABLE 2

| Sample | Ra(± nm) | Rq(± nm) | Surface Area (m²/g) |
|---|---|---|---|
| Micronized | 30.97 (12.25) | 45.07 (11.76) | 6.55 |
| Sample 3 | 53.79 (2.11) | 72.11 (1.35) | 10.79 |
| Sample 4 | 11.20 (1.55) | 16.52 (3.13) | 7.49 |

Surface roughness analysis of the samples suggested that sample 3 possessed the greatest surface roughness, whereas sample 4 (not prepared by the current invention) was the smoothest. Sample 3 had a greater surface area than the other samples, which may be related to the materials roughness. The $R_a$ and $R_q$ values, and the surface area of sample 3 are greater than the micronized sample and sample 4.

The standard deviation of the $R_a$ and $R_q$ values for the micronized sample is much greater than samples 3 and 4. This could indicate a greater variance of surface roughness for micronized sample than samples 3 and 4.

Figure 32:
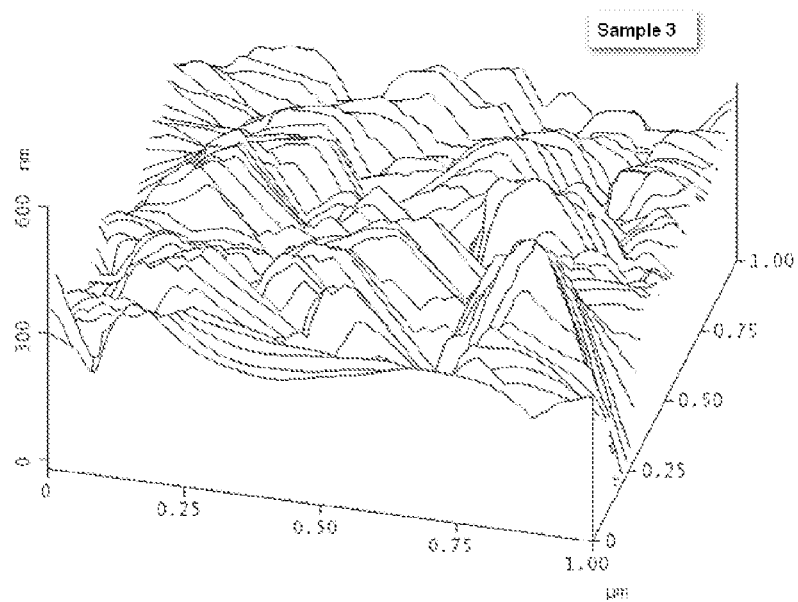
FIG. 32 shows AFM contour plots for surface roughness of sample 3 FP.
Figure 33:
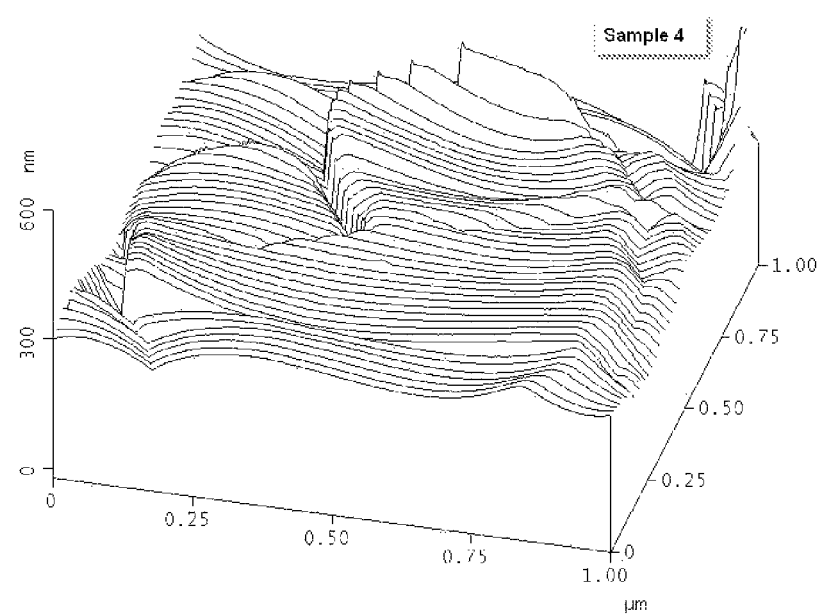
FIG. 33 shows AFM contour plots for surface roughness of sample 4 FP.

FIGS. 32 and 33 show AFM contour plots for surface roughness for samples 3 and 4 respectively. These show that sample 4 is much smoother than sample 3. The difference in the contour plots shows that sample 3 has a different surface roughness to sample 4 and this is reflected in the $R_a$ and $R_q$ values.

Example 8

A solution of Fenoterol hydrobromide (10 g) in methanol (200 mL) was prepared then and spray-dry with Buchi-B290 using twin-fluid nozzle with 0.7 mm orifice with a supporting nitrogen flow rate of 35-40 m³/h (100% Aspirator), at flow rate of 9 mL/min (30% Pump) and nozzle clean setting 2. Inlet temperature is 78° C. and outlet temperature 38° C. Diisopropyl ether (300 mL) was charged to a stirred 500 mL maximum volume ultrasonic vessel connected to the bottom of the B-290 cyclone and thermoregulated at 5° C. The spray dried product was collected into the ultrasonic vessel operating at 40 W continuous power for 2 hr, following the addition of the first particles of amorphous Fenoterol hydrobromide. The particles were recovered by spray drying the suspension with a Buchi-B290 as above with inlet temperature is 110° C. and outlet temperature 50° C. The data and particle SEM images for this example are shown in FIGS. 17-20.

Figure 17:
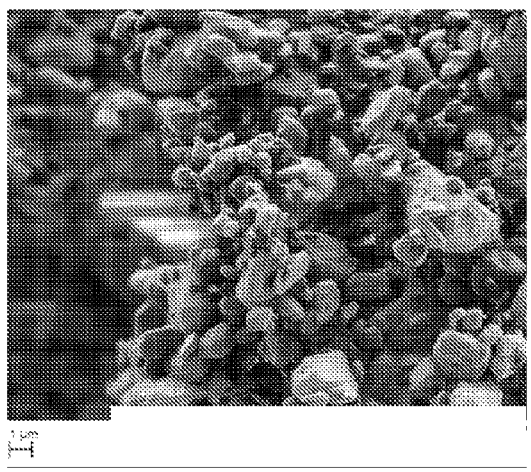
FIG. 17 Micronised Fenoterol hydrobromide.
Figure 18:
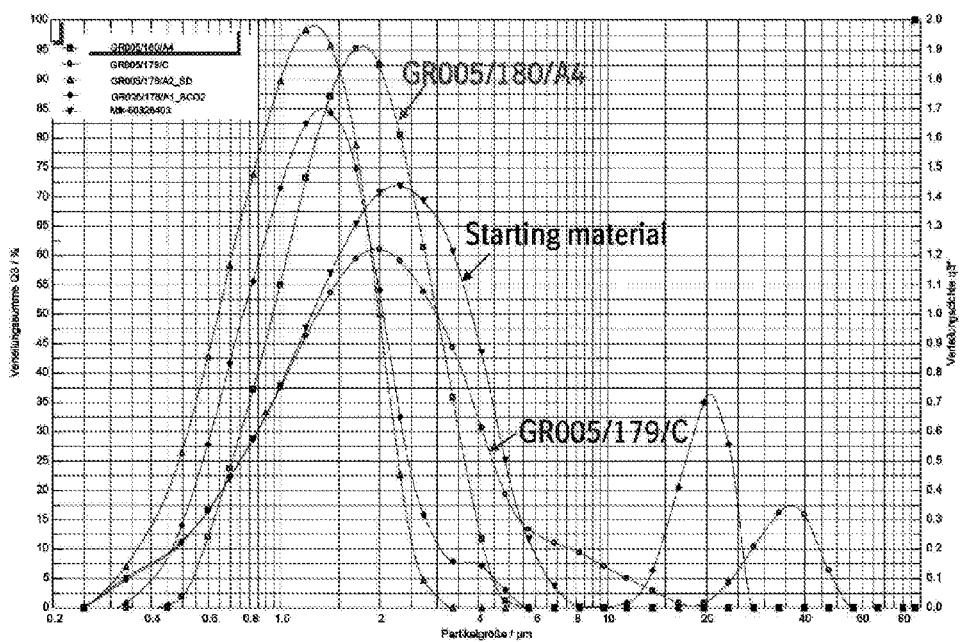
FIG. 18 Particle size distribution data GR005/180/A4 and GR005/179/C are particles prepared by this invention.

FIG. 17 shows an SEM image of commercial micronised Fenoterol hydrobromide. FIG. 18 shows the particle size distribution data for samples of particles processed by this invention namely GR005/180/A4 and GR005/179/C. FIG. 19 shows a comparative Fine Particle Fraction (FPF) data using a commercial HandiHaler inhalation device whereas test rig. Comparing the row for FPF [%] on FIGS. 19 and 20, the increase in FPF varied between 30 and 117%.

FIG. 21 shows the dispersive surface coverage v. surface energy for micronised Budesonide and Budesonide particles of the present invention. IGC was used to measure surface energy of the particles of this invention. IGC can be carried out with two sets of conditions. At finite dilution the adsorption isotherms can be derived from peak profiles and used to calculate adsorption energy distributions. Secondly at infinite dilution amount of solutes close to the detection limit of the instrument are injected and in this case the solute-solute interactions are small and only solute-sorbent interactions influence the measured retention time. Only limited adsorbance (coverage) at particularly high energy sites are analysed as shown on the left of FIG. 21. As the amount of solute is increased to finite dilution ultimately 100% coverage is achieved giving rise to adsorption on all sites of the particles regardless of varying surface energy. The particles of the invention are characterised by having isoenergetic distribution of surface energy as shown quite clearly in FIG. 21. The surface energy is very similar and near identical at both finite and infinite dilution for particles prepared by the preferred method of this inventions, whereas typical micronized particles show dramatic variances at finite and infinite dilution.

The invention claimed is:

1. A process for increasing the crystallinity of a crystallizable solid, comprising contacting said crystallizable solid with a non-solvent; and
   applying ultrasound to the crystallizable solid when in contact with said non-solvent;
   wherein the crystallizable solid is selected from the group consisting of an active pharmaceutical ingredient, an active agrochemical ingredient, a pharmaceutical excipient, an agrochemical excipient and appropriate mixtures of two or more thereof; and wherein the process further comprises:
   (i) forming a solution of the crystallizable solid in a solvent;
   (ii) subjecting the solution, after step (i), to a process selected from the group consisting of rapid precipitation, freeze drying, lyophilisation, rapid expansion of supercritical solutions, spray drying or mixtures thereof, wherein the said dissolved crystallizable solid is converted into a substantially dry solid material;
   (iii) isolating, after step (ii), the substantially dry crystallizable solid from the liquid and/or gaseous components of the process of step (ii);
   (iv) treating, after step (iii), said substantially dry crystallizable solid from step (iii) with a non-solvent therefor;
   (v) applying ultrasound, after step (iv), to the crystallizable solid from step (iv) when it is in contact with said non-solvent; and
   (vi) optionally, after step (v), separating and/or drying the resultant crystallizable solid from step (v).

2. A process according to claim 1, wherein the crystallizable solid is a particulate solid material having a mass median aerodynamic diameter of up to about 10 µm.

3. A process according to claim 1, wherein prior to the application of the above process, the crystallizable solid is less than 50% crystalline.

4. A process according to claim 1, wherein the crystallizable solid is a pharmaceutically active ingredient selected from the group consisting of anti-allergics, bronchodilators, anti-inflammatory steroids and mixtures thereof.

5. A process according to claim 1, wherein the crystallizable solid is obtained from spray-drying.

6. A process according to claim 1, wherein the crystallizable solid produced by the process is at least 90% crystalline.

\* \* \* \* \*